US007414067B2

(12) United States Patent
Boyd et al.

(10) Patent No.: US 7,414,067 B2
(45) Date of Patent: Aug. 19, 2008

(54) OPHTHALMIC COMPOSITIONS FOR TREATING OCULAR HYPERTENSION

(75) Inventors: Edward Andrew Boyd, Berkshire (GB); Michael H. Fisher, Ringoes, NJ (US); Maria L. Garcia, Edison, NJ (US); Gregory J. Kaczorowski, Edison, NJ (US); Peter T. Meinke, Plainfield, NJ (US); William H. Parsons, Belle Mead, NJ (US); Stephen Price, Hertford (GB); John Stibbard, Oxon (GB)

(73) Assignees: Merck & Co. Inc., Rahway, NJ (US); Evotec OAI (GB)

(*) Notice: Subject to any disclaimer, the term of this patent is extended or adjusted under 35 U.S.C. 154(b) by 432 days.

(21) Appl. No.: 10/542,169

(22) PCT Filed: Mar. 24, 2004

(86) PCT No.: PCT/US2004/009028

§ 371 (c)(1),
(2), (4) Date: Jul. 13, 2005

(87) PCT Pub. No.: WO2004/087051

PCT Pub. Date: Oct. 14, 2004

(65) Prior Publication Data

US 2006/0069256 A1    Mar. 30, 2006

Related U.S. Application Data

(60) Provisional application No. 60/458,103, filed on Mar. 27, 2003.

(51) Int. Cl.
*A61K 31/427* (2006.01)
*A61K 31/5377* (2006.01)
*C07D 277/20* (2006.01)
*C07D 403/02* (2006.01)
*C07D 413/02* (2006.01)

(52) U.S. Cl. .............. 514/371; 548/146; 548/190; 548/193; 548/194; 548/195; 544/106; 544/143; 544/224; 544/358; 544/373; 514/231.2; 514/232.8; 514/235.2; 514/252.13; 514/370

(58) Field of Classification Search .............. 544/224, 544/336, 358, 372, 373, 106, 111, 141, 143; 548/146, 190, 195; 514/365, 371, 235.2, 514/252.13
See application file for complete search history.

(56) References Cited

U.S. PATENT DOCUMENTS

| 3,336,194 A | 8/1967 | Shen |
| 3,338,921 A | 8/1967 | Shen |
| 3,501,465 A | 3/1970 | Shen et al. |
| 3,629,284 A | 12/1971 | Yamamoto et al. |
| 3,669,960 A | 6/1972 | Okamoto et al. |
| 4,277,489 A * | 7/1981 | Vandoni .................. 514/414 |
| 4,386,098 A | 5/1983 | Woltersdorf, Jr. et al. |
| 4,416,890 A | 11/1983 | Woltersdorf, Jr. et al. |
| 4,426,388 A | 1/1984 | Woltersdorf, Jr. et al. |
| 4,668,697 A | 5/1987 | Shepard et al. |
| 4,797,413 A | 1/1989 | Baldwin et al. |
| 4,824,857 A | 4/1989 | Goh et al. |
| 4,863,922 A | 9/1989 | Baldwin et al. |
| 4,883,819 A | 11/1989 | Bito |
| 5,001,153 A | 3/1991 | Ueno et al. |
| 5,153,192 A | 10/1992 | Dean et al. |
| 5,240,923 A | 8/1993 | Dean et al. |
| 5,378,703 A | 1/1995 | Dean et al. |
| 5,877,202 A | 3/1999 | Bitonti et al. |
| 5,925,342 A | 7/1999 | Adorante et al. |
| 6,218,418 B1 * | 4/2001 | Pevarello et al. ............ 514/404 |
| 6,545,036 B2 * | 4/2003 | Garcia et al. ................ 514/415 |
| 6,911,466 B2 * | 6/2005 | Koo et al. .................... 514/420 |
| 6,914,070 B2 * | 7/2005 | Garcia et al. ................ 514/415 |
| 7,034,049 B1 * | 4/2006 | Pevarello et al. ............ 514/404 |
| 7,037,929 B1 * | 5/2006 | Pevarello et al. ............ 514/371 |

FOREIGN PATENT DOCUMENTS

| EP | 0342 682 A2 | 5/1989 |
| WO | WO 89/10757 A1 | 11/1989 |
| WO | WO 94/21246 A1 | 9/1994 |
| WO | WO 94/28900 A1 | 12/1994 |
| WO | WO 96/25397 A1 | 8/1996 |
| WO | WO 96/33719 A1 | 10/1996 |
| WO | WO 00/40088 A1 | 7/2000 |
| WO | WO 01/52876 A1 | 7/2000 |
| WO | WO 02/065977 A2 | 8/2002 |

OTHER PUBLICATIONS

Pevarello et al (2000): STN International HCAPLUS database, (Columbus, Ohio), Accession No. 2000:314687.*
Koo et al (2001): STN International HCAPLUS database, (Columbus, Ohio), Accession No. 2001:780679.*
V. K. Boltze et al., Chemische Struktur und Antiphlogistische Wirkung in der Reihe der Substituierten Indol-3-Essigsauren, 1980, pp. 1314-1325, vol. 30, Drug Research.
G. Linari et al., "Substituted Anilides of 1-(p-Chlorobenzoly)-5-Methoxy-2Mehtyl-Indole-3-Acetic", 1973, vol. 23, No. 1, Drug Research.
A. M. Harman et al., "Development and Aging of Cell Topography in the Human Retinal Pigment Epithelium", 1997, pp. 2016-2026, vol. 38, No. 10, Investigative Ophthalmology & Visual Science.

(Continued)

*Primary Examiner*—Golam M Shameem
(74) *Attorney, Agent, or Firm*—Sylvia A. Ayler; William Krovatin

(57) ABSTRACT

This invention relates to the use of potent potassium channel blockers or a formulation thereof in the treatment of glaucoma and other conditions which leads to elevated intraoccular pressure in the eye of a patient. This invention also relates to the use of such compounds to provide a neuroprotective effect to the eye of mammalian species, particularly humans.

15 Claims, No Drawings

OTHER PUBLICATIONS

E. L. Eliel et al.,"Chirality in Molecules Devoid of Chiral Centers", 1994, pp. 1119-1190, Stereochemistry of Organic Compounds.

R. A. Schumer et al., "The Nerve of Glaucoma!", 1994, pp. 37-44, vol. 112, Arch Ophthalmol.

L. Dandona et al., "Selective Effects of experimental Glaucoma on Axonal Transport by Retinal Ganglion Cells to the Dorsal Lateral Geniculate Nucleus", 1991, pp. 1593-1599, vol. 32, No. 5, Investigative Ophthalmology & Visual Science.

S. M. Berge, "Pharmaceutical Salts", 1977, pp. 1-19, vol. 66, No. 1, J. of Pharmaceutical Sciences.

K. Cardwell et al., "Methods for Indole Alkaloid Synthesis: A Study of the Compaitbility of the Indole-2,3-Quinodimethane Strategy for the Synthesis of 16-Methoxy-Substituted Aspidosperama—Type Alkaloids. Synthesis of (+)-and (−)-16-Methoxytabersonine", 1988, pp. 2242-2248, vol. 110, J. Am. Chem. Soc.

E. Shaw, "The Synthesis of Tryptamines Related to Serotonin", 1955, pp. 4319-4323, vol. 77, J. Am. Chem. Soc.

T.Y. Shen et al., "Non-Steroid Anti-Inflammatory Agents", 1963, pp. 488-489, vol. 85, J. Am. Chem. Soc.

* cited by examiner

OPHTHALMIC COMPOSITIONS FOR TREATING OCULAR HYPERTENSION

CROSS REFERENCE TO RELATED APPLICATIONS

This application is the National Stage of International Application No. PCT/US04/009028 filed on Mar. 24, 2004, which claims the benefit under 35 U.S.C. 119(e) of U.S. Provisional Application No. 60/458,103 filed on Mar. 27, 2003.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Many of the drugs formerly used to treat glaucoma proved unsatisfactory. The early methods of treating glaucoma employed pilocarpine and produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilizing activity, that become more apparent with increased doses and render them unacceptable for chronic ocular use and can also cause cardiovascular effects.

Although pilocarpine and β-adrenergic antagonists reduce intraocular pressure, none of these drugs manifests its action by inhibiting the enzyme carbonic anhydrase, and thus they do not take advantage of reducing the contribution to aqueous humor formation made by the carbonic anhydrase pathway.

Agents referred to as carbonic anhydrase inhibitors decrease the formation of aqueous humor by inhibiting the enzyme carbonic anhydrase. While such carbonic anhydrase inhibitors are now used to treat intraocular pressure by systemic and topical routes, current therapies using these agents, particularly those using systemic routes are still not without undesirable effects. Because carbonic anhydrase inhibitors have a profound effect in altering basic physiological processes, the avoidance of a systemic route of administration serves to diminish, if not entirely eliminate, those side effects caused by inhibition of carbonic anhydrase such as metabolic acidosis, vomiting, numbness, tingling, general malaise and the like. Topically effective carbonic anhydrase inhibitors are disclosed in U.S. Pat. Nos. 4,386,098; 4,416,890; 4,426,388; 4,668,697; 4,863,922; 4,797,413; 5,378,703, 5,240,923 and 5,153,192.

Prostaglandins and prostaglandin derivatives are also known to lower intraocular pressure. U.S. Pat. No. 4,883,819 to Bito describes the use and synthesis of PGAs, PGBs and PGCs in reducing intraocular pressure. U.S. Pat. No. 4,824,857 to Goh et al. describes the use and synthesis of PGD2 and derivatives thereof in lowering intraocular pressure including derivatives wherein C-10 is replaced with nitrogen. U.S. Pat. No. 5,001,153 to Ueno et al. describes the use and synthesis of 13,14-dihydro-15-keto prostaglandins and prostaglandin derivatives to lower intraocular pressure. U.S. Pat. No. 4,599,353 describes the use of eicosanoids and eicosanoid derivatives including prostaglandins and prostaglandin inhibitors in lowering intraocular pressure. Prostaglandin and prostaglandin derivatives lower intraocular pressure by increasing uveoscieral outflow. This is true for both the F type and A type of Pgs and hence presumably also for the B, C, D, E and J types of prostaglandins and derivatives thereof. A problem with using prostaglandin derivatives to lower intraocular pressure is that these compounds often induce an initial increase in intraocular pressure, can change the color of eye pigmentation and cause proliferation of some tissues surrounding the eye.

As can be seen, there are several current therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to the use of potent potassium channel blockers or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using novel indole compounds having the structural formula I:

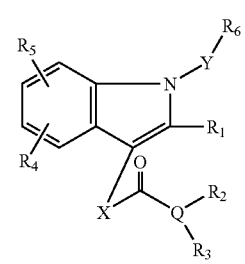

Formula I or a pharmaceutically acceptable salt, enantiomer, diastereomer or mixture thereof:

wherein,

R represents hydrogen, or $C_{1-6}$ alkyl;

$R_1$ represents hydrogen or $C_{1-6}$ alkyl, $CF_3$, $C_{1-6}$ alkoxy, OH, $COR^e$, $CO_2R_8$, $CONHCH_2CO_2R$, $N(R)_2$, said alkyl and alkoxy optionally substituted with 1-3 groups selected from $R^b$;

X represents —$(CHR_7)_p$—;

Y is not present, —$CO(CH_2)_n$—, or —$CH(OR)$—;

Q represents N, $CR^y$, or O, wherein $R_2$ is absent when Q is O;

$R^y$ represents H, or $C_{1-6}$ alkyl;

$R_w$ represents H, $C_{1-6}$ alkyl, —C(O)$C_{1-6}$ alkyl, —C(O)O$C_{1-6}$ alkyl, —SO$_2$N(R)$_2$, —SO$_2$C$_{1-6}$ alkyl, —SO$_2$C$_{6-10}$ aryl, NO$_2$, CN or —C(O)N(R)$_2$;

$R_2$ represents hydrogen, $C_{1-10}$ alkyl, $C_{1-6}$ alkylSR, —(CH$_2$)$_n$O(CH$_2$)$_m$OR, —(CH$_2$)$_n$C$_{1-6}$ alkoxy, —(CH$_2$)$_n$C$_{3-8}$ cycloalkyl, —(CH$_2$)$_n$C$_{3-10}$ heterocyclyl, —(CH$_2$)$_n$C$_{5-10}$ heteroaryl, —N(R)$_2$, —COOR, or —(CH$_2$)$_n$C$_{6-10}$ aryl, said alkyl, heterocyclyl, aryl or heteroaryl optionally substituted with 1-3 groups selected from $R^a$;

$R_3$ represents hydrogen, $C_{1-10}$ alkyl, —(CH$_2$)$_n$C$_{3-8}$ cycloalkyl, —(CH$_2$)$_n$C$_{3-10}$ heterocyclyl, —(CH$_2$)$_n$C$_{5-10}$ heteroaryl, —(CH$_2$)$_n$COOR, —(CH$_2$)$_n$C$_{6-10}$ aryl, —(CH$_2$)$_n$NHR$_8$, —(CH$_2$)$_n$N(R)$_2$, —(CH$_2$)$_n$N(R$_8$)$_2$, —(CH$_2$)$_n$NHCOOR, —(CH$_2$)$_n$N(R$_8$)CO$_2$R, —(CH$_2$)$_n$N(R$_8$)COR, —(CH$_2$)$_n$NHCOR, —(CH$_2$)$_n$CONH(R$_8$), aryl, —(CH$_2$)$_n$C$_{1-6}$—OR, CF$_3$, —(CH$_2$)$_n$SO$_2$R, —(CH$_2$)$_n$SO$_2$N(R)$_2$, —(CH$_2$)$_n$CON(R)$_2$, —(CH$_2$)$_n$CONHC(R)$_3$, —(CH$_2$)$_n$CONHC(R)$_2$CO$_2$R, —(CH$_2$)$_n$COR$_8$, nitro, cyano or halogen, said alkyl, alkoxy, heterocyclyl, aryl or heteroaryl optionally substituted with 1-3 groups of $R^a$;

or, when Q is N, $R_2$ and $R_3$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;

$R_4$ and $R_5$ independently represent hydrogen, $C_{1-6}$ alkoxy, OH, $C_{1-6}$ alkyl, COOR, SO$_3$H, $C_{1-6}$ alkylcarbonyl, S(O)$_q$R$^y$, —O(CH$_2$)$_n$N(R)$_2$, —O(CH$_2$)$_n$CO$_2$R, —OPO(OH)$_2$, CF$_3$, —N(R)$_2$, nitro, cyano, $C_{1-6}$ alkylamino, or halogen;

$R_6$ represents hydrogen, $C_{1-10}$ alkyl, —(CH$_2$)$_n$C$_{6-10}$ aryl, —NH(CH$_2$)$_n$C$_{6-10}$ aryl, —(CH$_2$)$_n$C$_{5-10}$ heteroaryl, —NH(CH$_2$)$_n$C$_{5-10}$ heteroaryl, (C$_{6-10}$ aryl)O—, —(CH$_2$)$_n$C$_{3-10}$ heterocyclyl, —(CH$_2$)$_n$C$_{3-8}$ cycloalkyl, —COOR, —C(O)CO$_2$R, said aryl, heteroaryl, heterocyclyl and alkyl optionally substituted with 1-3 groups selected from $R^a$;

$R_7$ represents hydrogen, $C_{1-6}$ alkyl, —(CH$_2$)$_n$COOR or —(CH$_2$)$_n$N(R)$_2$;

$R_8$ represents —(CH$_2$)$_n$C$_{3-8}$ cycloalkyl, —(CH$_2$)$_{n\ 3-10}$ heterocyclyl, $C_{1-6}$ alkoxy or —(CH$_2$)$_n$C$_{5-10}$ heteroaryl, —(CH$_2$)$_n$C$_{6-10}$ aryl said heterocyclyl, aryl or heteroaryl optionally substituted with 1-3 groups selected from $R^a$;

$R^a$ represents F, Cl, Br, I, CF$_3$, N(R)$_2$, NO$_2$, CN, —(CH$_2$)$_n$COR$_8$, —(CH$_2$)$_n$CONHR$_8$, —(CH$_2$)$_n$CON(R$_8$)$_2$, —O(CH$_2$)$_n$COOR, —NH(CH$_2$)$_n$OR, —COOR, —OCF$_3$, —NHCOR, —SO$_2$R, —SO$_2$NR$_2$, —SR, (C$_1$-C$_6$ alkyl)O—, —(CH$_2$)$_n$O(CH$_2$)$_m$OR, —(CH$_2$)$_n$C$_{1-6}$ alkoxy, (aryl)O—, —OH, (C$_1$-C$_6$ alkyl)S(O)$_m$—, H$_2$N—C(NH)—, (C$_1$-C$_6$ alkyl)C(O)—, (C$_1$-C$_6$ alkyl)OC(O)NH—, —(C$_1$-C$_6$ alkyl)NR$_w$(CH$_2$)$_n$C$_{3-10}$ heterocyclyl-R$_w$, —(C$_1$-C$_6$ alkyl)O(CH$_2$)$_n$C$_{3-10}$ heterocyclyl-R$_w$, —(C$_1$-C$_6$ alkyl)S(CH$_2$)$_n$C$_{3-10}$ heterocyclyl-R$_w$, —(C$_1$-C$_6$ alkyl)-C$_{3-10}$ heterocyclyl-R$_w$, —(CH$_2$)$_n$—Z$^1$—C(=Z$^2$)N(R)$_2$, —(C$_{2-6}$ alkenyl)NR$_w$(CH$_2$)$_n$C$_{3-10}$ heterocyclyl-R$_w$, —(C$_{2-6}$ alkenyl)O(CH$_2$)$_n$C$_{3-10}$ heterocyclyl-R$_w$, —(C$_{2-6}$ alkenyl)S(CH$_2$)$_n$C$_{3-10}$ heterocyclyl-R$_w$, —(C$_{2-6}$ alkenyl)-C$_{3-10}$ heterocyclyl-R$_w$, —(C$_{2-6}$ alkenyl)-Z$^1$—C(=Z$^2$)N(R)$_2$, —(CH$_2$)$_n$SO$_2$R, —(CH$_2$)$_n$SO$_3$H, —(CH$_2$)$_n$PO(OR)$_2$, cyclohexyl, morpholinyl, piperidyl, pyrrolidinyl, thiophenyl, phenyl, pyridyl, imidazolyl, oxazolyl, isoxazolyl, thiazolyl, thienyl, furyl, isothiazolyl, C$_{2-6}$ alkenyl, and C$_1$-C$_{10}$ alkyl, said alkyl, alkenyl, alkoxy, phenyl, pyridyl, imidazolyl, oxazolyl, isoxazolyl, thiazolyl, thienyl, furyl, and isothiazolyl optionally substituted with 1-3 groups selected from C$_1$-C$_6$ alkyl, and COOR;

$Z^1$ and $Z^2$ independently represents NR$_w$, O, CH$_2$, or S;

$R^b$ represents $C_{1-6}$ alkyl, —COOR, —SO$_3$R, —OPO(OH)$_2$, —(CH$_2$)$_n$C$_{6-10}$ aryl, or —(CH$_2$)$_n$C$_{5-10}$ heteroaryl;

$R^c$ represents hydrogen, $C_{1-6}$ alkyl, or —(CH$_2$)$_n$C$_{6-10}$ aryl;

m is 0-3;

n is 0-3;

q is 0-2; and p is 0-1.

This and other aspects of the invention will be realized upon inspection of the invention as a whole.

DETAILED DESCRIPTION OF THE INVENTION

The present invention is directed to novel potassium channel blockers of Formula I. It also relates to a method for decreasing elevated intraocular pressure or treating glaucoma by administration, preferably topical or intra-camaral administration, of a composition containing a potassium channel blocker of Formula I described hereinabove and a pharmaceutically acceptable carrier.

In an embodiment of the instant invention are the compounds wherein X represents CHR$_7$.

Another embodiment of this invention is realized when Y is —CO(CH$_2$)$_n$ and all other variables are as originally described. A subembodiment of this invention is realized when n is 0.

Another embodiment of this invention is realized when Y is CH(OR) and all other variables are as originally described.

Still another embodiment of this invention is realized when Q is N and all other variables are as originally described.

Still another embodiment of this invention is realized when Q is CH and all other variables are as originally described.

In another embodiment R$_w$ is selected from H, C$_{1-6}$ alkyl, —C(O)C$_{1-6}$ alkyl and —C(O)N(R)$_2$.

Still another embodiment of this invention is realized when R$_6$ is (CH$_2$)$_n$C$_{6-10}$ aryl, (CH$_2$)$_n$C$_{5-10}$ heteroaryl, (CH$_2$)$_n$C$_{3-10}$ heterocyclyl, or (CH$_2$)$_n$C$_{3-8}$ cycloalkyl, said aryl, heteroaryl, heterocyclyl and cycloalkyl optionally substituted with 1 to 3 groups of $R^a$, and all other variables are as originally described.

Yet another embodiment of this invention is realized when R$_6$ is (CH$_2$)$_n$C$_{6-10}$ aryl, (CH$_2$)$_n$C$_{5-10}$ heteroaryl or (CH$_2$)$_n$C$_{3-10}$ heterocyclyl, said aryl, heteroaryl and heterocyclyl optionally substituted with 1 to 3 groups of $R^a$, and all other variables are as originally described.

Yet another embodiment of this invention is realized when R$_7$ is hydrogen or C$_{1-6}$ alkyl, and all other variables are as originally described.

Yet another embodiment of this invention is realized when Y is —CO(CH$_2$)$_n$, and Q is N. A subembodiment of this invention is realized when n is 0.

Still another embodiment of this invention is realized when Y is —CO(CH$_2$)$_n$, Q is N, R$_2$ is C$_{1-10}$ alkyl or C$_{1-6}$ alkylOH and R$_3$ is (CH$_2$)$_n$C$_{3-10}$ heterocyclyl, said heterocyclyl and alkyl optionally substituted with 1 to 3 groups of $R^a$. A subembodiment of this invention is realized when n is 0.

Another embodiment of the instant invention is realized when $R^a$ is selected from F, Cl, Br, I, CF$_3$, N(R)$_2$, NO$_2$, CN, —CONHR$_8$, —CON(R$_8$)$_2$, —O(CH$_2$)$_n$COOR, —NH(CH$_2$)$_n$OR, —COOR, —OCF$_3$, —NHCOR, —SO$_2$R, —SO$_2$NR$_2$, —SR, (C$_1$-C$_6$ alkyl)O—, —(CH$_2$)$_n$O(CH$_2$)$_m$OR, —(CH$_2$)$_n$C$_{1-6}$ alkoxy, (aryl)O—, —OH, (C$_1$-C$_6$ alkyl)S(O)$_m$—, H$_2$N—C(NH)—, (C$_1$-C$_6$ alkyl)C(O)—, (C$_1$-C$_6$ alkyl)OC(O)NH—, —(C$_1$-C$_6$ alkyl)NR$_w$(CH$_2$)$_n$C$_{3-10}$ heterocyclyl-R$_w$, —(CH$_2$)$_n$—Z$^1$—C(=Z$^2$)N(R)$_2$, —(C$_{2-6}$ alkenyl)NR$_w$(CH$_2$)$_n$C$_{3-10}$ heterocyclyl-R$_w$, —(C$_{2-6}$ alkenyl)-Z$^1$—C(=Z$^2$)N(R)$_2$, —(CH$_2$)$_n$SO$_2$R, —(CH$_2$)$_n$SO$_3$H, —(CH$_2$)$_n$PO(OR)$_2$, C$_{2-6}$ alkenyl, and C$_1$-C$_{10}$ alkyl, said alkyl and alkenyl, optionally substituted with 1-3 groups selected from C$_1$-C$_6$ alkyl, and COOR;

Still another embodiment of this invention is realized when $R_2$ and $R_3$ are taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$. Examples of said heterocyclic groups are:

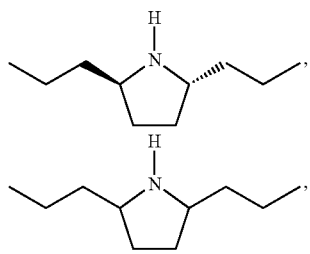

and the like.

Examples of compounds to be used in this invention are found in Tables 1 through 4:

TABLE 1

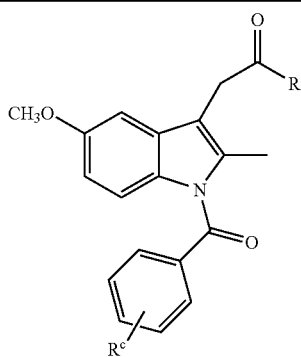

Wherein R represents:

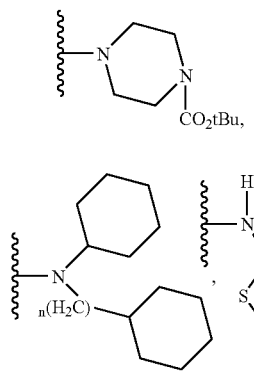
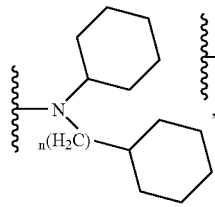
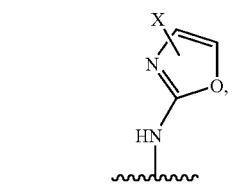

TABLE 1-continued

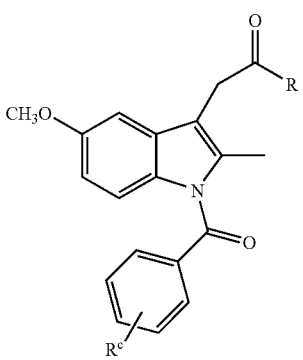

Wherein R represents:

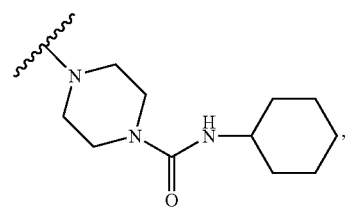
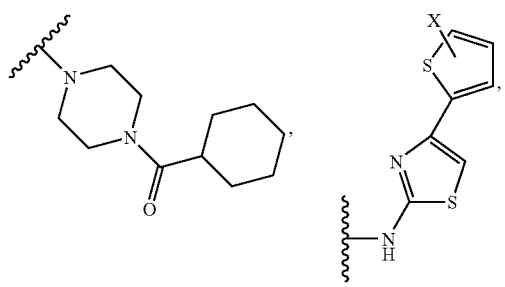

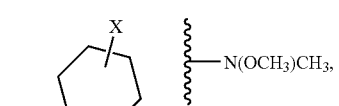

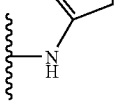  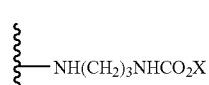

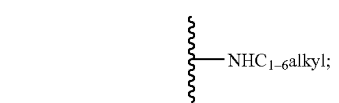

n is 0 to 3;

X, Y and Z, independently represent hydrogen or $C_{1-6}$ alkyl; and

Rc represents hydrogen, halogen, $C_{1-6}$ alkyl, CF3, OCF3, N(CH3)3, $COC_{1-6}$ alkyl, or methoxy;

TABLE 2
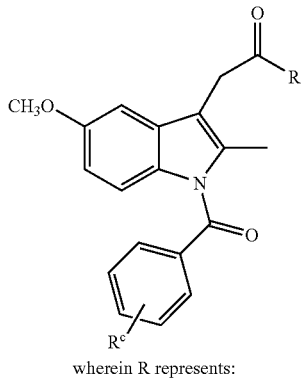
wherein R represents:
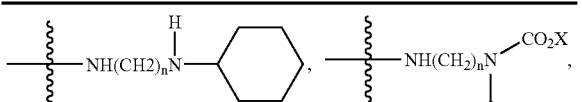
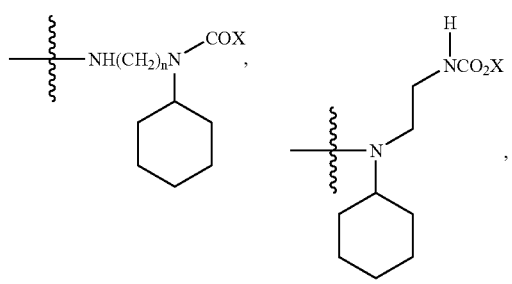
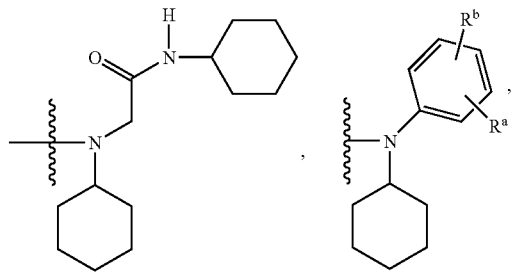
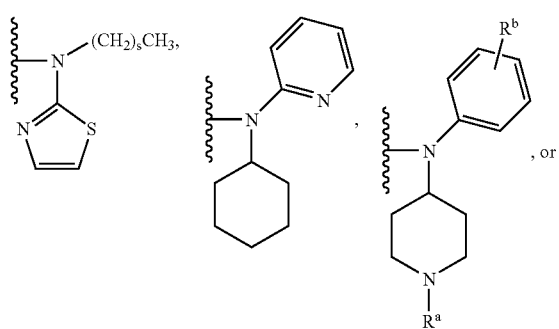
TABLE 2-continued
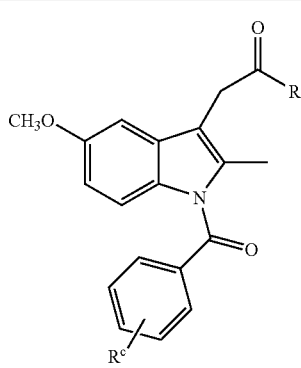
wherein R represents:
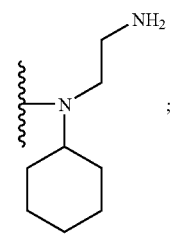
n is 0 to 3; s is 1-5;
X represents hydrogen or $C_{1-6}$ alkyl;
$R^b$ and $R^a$ independently represent hydrogen, methoxy, $CO_2X$, NHAc, or $C_{1-6}$ alkyl;
$R^c$ represents hydrogen, halogen, $C_{1-6}$ alkyl, $CF_3$, $OCF_3$, $N(CH_3)_2$, $COC_{1-6}$ alkyl, or methoxy
TABLE 3
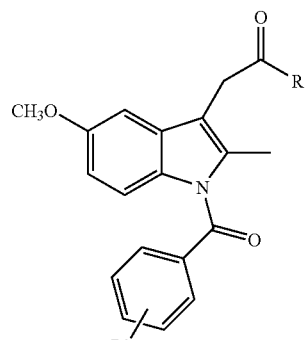
wherein R represents:
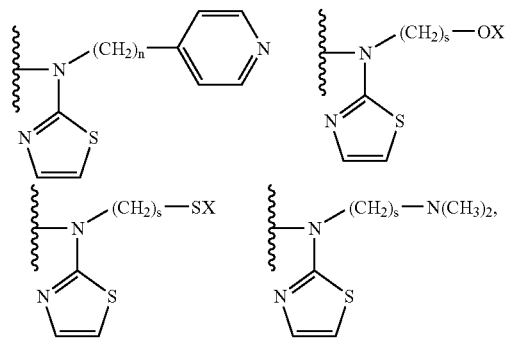

TABLE 3-continued

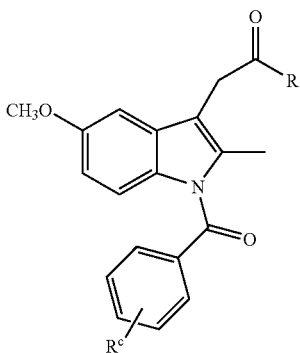

wherein R represents:

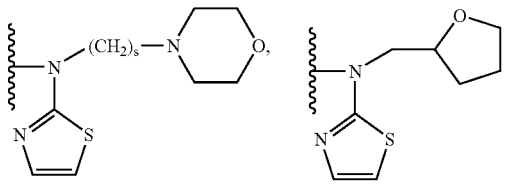

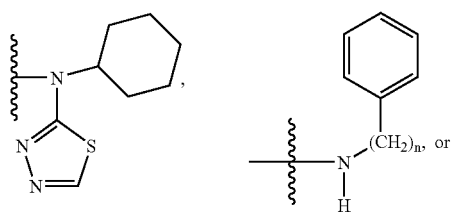

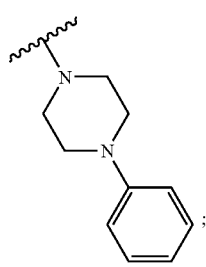

n is 0 to 3; s is 1-5;
X represents hydrogen or $C_{1-6}$ alkyl; and
$R^c$ represents hydrogen, halogen, $C_{1-6}$ alkyl, $CF_3$, $OCF_3$, $N(CH_3)_2$, $COC_{1-6}$ alkyl, or methoxy

TABLE 4

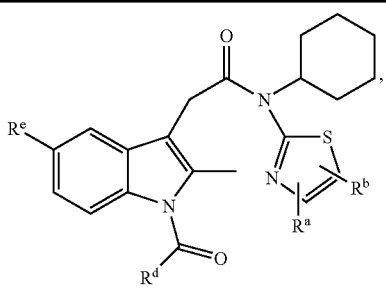

TABLE 4-continued

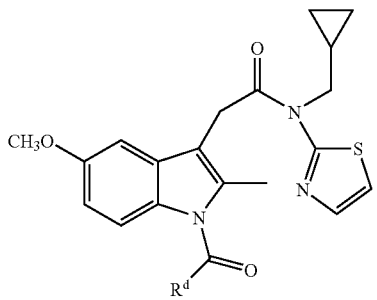

or

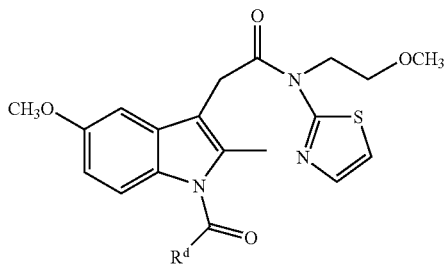

wherein:
$R^b$ and $R^a$ independently represent hydrogen, methoxy, $CO_2X$, NHAc, or $C_{1-6}$ alkyl;
$R^d$ represents C1-6 alkyl, pyridinyl, —O-phenyl, phenyl, thienyl, said pyridinyl and phenyl optionally substituted with 1-3 halogen, $CF_3$, $OCF_3$, $N(CH_3)_2$, methoxy or C1-6 alkyl; and
$R^e$ represents methoxy, $O(CH_2)_2N(CH_3)_2$, or OH; or a pharmaceutically acceptable salt, enantiomer, diastereomer or mixture thereof.

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

When any variable (e.g. aryl, heterocycle, $R^1$, $R^6$ etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

Cycloalkyl is a specie of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Examples of aryl groups are phenyl, naphthyl, tetrahydronaphthyl, indanyl, biphenyl, phenanthryl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, dihydropyrrolyl, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from 2-azepinonyl, benzimidazolyl, 2-diazapinonyl, dihydroimidazolyl, dihydropyrolyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl. Additional nitrogen atoms may be present together with the first nitrogen and oxygen or sulfur, giving, e.g., thiadiazole.

This invention is also concerned with a method of treating ocular hypertension or glaucoma by administering to a patient in need thereof one of the compounds of formula I in combination with a β-adrenergic blocking agent such as timolol, a parasympathomimetic agent such as pilocarpine, carbonic anhydrase inhibitor such as dorzolamide, acetazolamide, metazolamide or brinzolamide, a prostaglandin such as latanoprost, rescula, S1033 or a prostaglandin derivative such as a hypotensive lipid derived from PGF2α prostaglandins. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2a}$ 1-$OCH_3$), or a hydroxy group ($PGF_{2a}$ 1-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, smooth muscle and epithelial tissues and which are gated by membrane potential and intracellular $Ca^{2+}$.

Intraocular pressure (IOP) is controlled by aqueous humor dynamics. Aqueous humor is produced at the level of the non-pigmented ciliary epithelium and is cleared primarily via outflow through the trabecular meshwork. Aqueous humor inflow is controlled by ion transport processes. It is thought that maxi-K channels in non-pigmented ciliary epithelial cells indirectly control chloride secretion by two mechanisms; these channels maintain a hyperpolarized membrane potential (interior negative) which provides a driving force for chloride efflux from the cell, and they also provide a counter ion ($K^+$) for chloride ion movement. Water moves passively with KCl allowing production of aqueous humor. Inhibition of maxi-K channels in this tissue would diminish inflow. Maxi-K channels have also been shown to control the contractility of certain smooth muscle tissues, and, in some cases, channel blockers can contract quiescent muscle, or increase the myogenic activity of spontaneously active tissue. Contraction of ciliary muscle would open the trabecular meshwork and stimulate aqueous humor outflow, as occurs with pilocarpine. Therefore maxi-K channels could profoundly influence aqueous humor dynamics in several ways; blocking this channel would decrease IOP by affecting inflow or outflow processes or by a combination of affecting both inflow/outflow processes.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration.

Macular edema is swelling within the retina within the critically important central visual zone at the posterior pole of the eye. An accumulation of fluid within the retina tends to detach the neural elements from one another and from their local blood supply, creating a dormancy of visual function in the area.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37-44; Investigative Ophthamol. & Visual Science, 32, 5, April 1991, pp. 1593-99. It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

As indicated above, potassium channel antagonists are useful for a number of physiological disorders in mammals, including humans. Ion channels, including potassium channels, are found in all mammalian cells and are involved in the modulation of various physiological processes and normal cellular homeostasis. Potassium ions generally control the resting membrane potential, and the efflux of potassium ions causes repolarization of the plasma membrane after cell depolarization. Potassium channel antagonists prevent repolarization and enable the cell to stay in the depolarized, excited state.

There are a number of different potassium channel subtypes. Physiologically, one of the most important potassium channel subtypes is the Maxi-K channel which is present in neuronal tissue, smooth muscle and epithelial tissue. Intracellular calcium concentration ($Ca^{2+}_i$) and membrane potential gate these channels. For example, Maxi-K channels are opened to enable efflux of potassium ions by an increase in the intracellular $Ca^{2+}$ concentration or by membrane depolarization (change in potential). Elevation of intracellular calcium concentration is required for neurotransmitter release. Modulation of Maxi-K channel activity therefore affects transmitter release from the nerve terminal by controlling membrane potential, which in turn affects the influx of extracellular $Ca^{2+}$ through voltage-gated calcium channels. The compounds of the present invention are therefore useful in the treatment of neurological disorders in which neurotransmitter release is impaired.

A number of marketed drugs function as potassium channel antagonists. The most important of these include the compounds Glyburide, Glipizide and Tolbutamide. These potassium channel antagonists are useful as antidiabetic agents. The compounds of this invention may be combined with one or more of these compounds to treat diabetes.

Potassium channel antagonists are also utilized as Class 3 antiarrhythmic agents and to treat acute infarctions in humans. A number of naturally occuring toxins are known to block potassium channels including Apamin, Iberiotoxin, Charybdotoxin, Noxiustoxin, Kaliotoxin, Dendrotoxin(s), mast cell degranuating (MCD) peptide, and β-Bungarotoxin (β-BTX). The compounds of this invention may be combined with one or more of these compounds to treat arrhythmias.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Alzheimer's disease is a neurodegenerative disease of the brain leading to severely impaired cognition and functionality. This disease leads to progressive regression of memory and learned functions. Alzheimer's disease is a complex disease that affects cholinergic neurons, as well as serotonergic, noradrenergic and other central neurotransmitter systems. Manifestations of Alzheimer's disease extend beyond memory loss and include personality changes, neuromuscular changes, seizures, and occasionally psychotic features.

Alzheimer's disease is the most common type of dementia in the United States. Some estimates suggest that up to 47% of those older than 85 years have Alzheimer's disease. Since the average age of the population is on the increase, the frequency of Alzheimer's disease is increasing and requires urgent attention. Alzheimer's is a difficult medical problem because there are presently no adequate methods available for its prevention or treatment.

Three classes of drugs are being investigated for the treatment of Alzheimer's disease. The first class consists of compounds that augment acetylcholine neurotransmitter function. Currently, cholinergic potentiators such as the anticholinesterase drugs are being used in the treatment of Alzheimer's disease. In particular, physostigmine (eserine), an inhibitor of acetylcholinesterase, has been used in its treatment. The administration of physostigmine has the drawback of being considerably limited by its short half-life of effect, poor oral bioavailability, and severe dose-limiting side-effects, particularly towards the digestive system. Tacrine (tetrahydroaminocridine) is another cholinesterase inhibitor that has been employed; however, this compound may cause hepatotoxicity.

A second class of drugs that are being investigated for the treatment of Alzheimer's disease is nootropics that affect neuron metabolism with little effect elsewhere. These drugs improve nerve cell function by increasing neuron metabolic activity. Piracetam is a nootropic that may be useful in combination with acetylcholine precursors and may benefit Alzheimer's patients who retain some quantity of functional acetylcholine release in neurons. Oxiracetam is another related drug that has been investigated for Alzheimer treatment.

A third class of drugs is those drugs that affect brain vasculature. A mixture of ergoloid mesylates is used for the treatment of dementia. Ergoloid mesylates decrease vascular resistance and thereby increase cerebral blood flow. Also employed are calcium channel blocking drugs including Nimodipine which is a selective calcium channel blocker that affects primarily brain vasculature.

Other miscellaneous drugs are targeted to modify other defects found in Alzheimer's disease. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Side effects of neuroleptics range from drowsiness and anti cholinergic effects to extrapyramidal side effects; other side effects of these drugs include seizures, inappropriate secretion of antidiuretic hormone, jaundice, weight gain and increased confusion. Anxiolytics, which are mild tranquilizers, are less effective than neuroleptics, but also have milder side effects. Use of these behavior-affecting drugs, however, remains controversial. The present invention is related to novel compounds which are useful as potassium channel antagonists. It is believed that certain diseases such as depression, memory disorders and Alzheimers disease are the result of an impairment in neurotransmitter release. The potassium channel antagonists of the present invention may therefore be utilized as cell excitants which should stimulate an unspecific release of neurotransmitters such as acetylcholine, serotonin and dopamine. Enhanced neurotransmitter release should reverse the symptoms associated with depression and Alzheimers disease.

The compounds within the scope of the present invention exhibit potassium channel antagonist activity and thus are useful in disorders associated with potassium channel malfunction. A number of cognitive disorders such as Alzheimer's Disease, memory loss or depression may benefit from enhanced release of neurotransmitters such as serotonin, dopamine or acetylcholine and the like. Blockage of Maxi-K channels maintains cellular depolarization and therefore enhances secretion of these vital neurotransmitters.

The compounds of this invention may be combined with anticholinesterase drugs such as physostigmine (eserine) and Tacrine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamin, Iberiotoxin, Charybdotoxin, Noxiustoxin, Kaliotoxin, Dendrotoxin(s), mast cell degranuating (MCD) peptide, β-Bungarotoxin (β-BTX) or a combination thereof in treating arrythmias. The compounds of this invention may further be combined with Glyburide, Glipizide, Tolbutamide or a combination thereof to treat diabetes.

The herein examples illustrate but do not limit the claimed invention. Each of the claimed compounds are potassium channel antagonists and are thus useful in the decribed neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The maxi-K channel blockers used can be administered in a therapeutically effective amount intravaneously, subcutaneously, topically, transdermally, parenterally or any other method known to those skilled in the art.

Ophthalmic pharmaceutical compositions are preferably adapted for topical administration to the eye in the form of solutions, suspensions, ointments, creams or as a solid insert. Ophthalmic formulations of this compound may contain from 0.01 to 5% and especially 0.5 to 2% of medicament. Higher dosages as, for example, about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mamalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples given by way of illustration is demonstrative of the present invention.

PREPARATIVE EXAMPLE 1

Synthesis of 6-OMe-indole

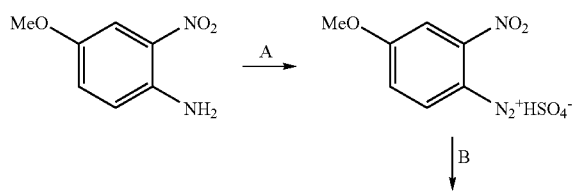

-continued

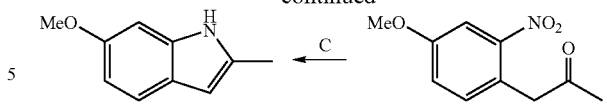

Step A

Adapted from ref: Magnus et al., J. Am. Chem. Soc. 110, 7, 2243, 1988.

4-Methoxy-2-nitro-aniline (35 g—Aldrich) was suspended in 250 mL of ethanol followed by addition of 14 mL of concentrated sulfuric acid. The suspension was cooled to 0° C., followed by slow addition of isoamyl nitrite (34 mL). After complete addition of isoamyl nitrite, the reaction mixture was stirred at 0 C for 1.5 h at which point a thick white slurry resulted. The reaction mixture was filtered and the precipitate was washed with 200 mL of cold ethanol followed by washing with 500 mL of ether. The filter cake was sucked dry under reduced pressure. 52 g of a free flowing powder was collected and used in the next step directly.

Step B

A 1 L flask was charged with isopropenyl acetate (75 mL), acetone (400 mL), 0.25 M HCl (250 mL), Cu (II)Cl$_2$ (4 g) and LiCl (15 g). This was cooled to 0 C followed by portionwise addition of the diazonium salt obtained above. The reaction mixture was vented throughout the 18 h reaction time. The reaction mixture was concentrated to a viscous oil, diluted with ethyl acetate (200 mL) and washed with water (50 mL). The organic phase was collected, dried and concentrated to an orange-reddish oil which subjected to purification by SGC to provide colorless low melting product (16 g) LCMS=[M+H] 209

Step C

Compound obtained in step B was taken up in 200 mL of ethyl acetate followed by addition of 20 g of Raney Nickel (previously washed with ethyl acetate). The reaction mixture was subjected to reduction with hydrogen at atmospheric pressure for 12 h. After TLC analysis indicated complete conversion, the reaction mixture was filtered over a pad of celite and this was washed thoroughly with ethyl acetate and methanol. The combined organic extracts were concentrated to provide crystalline white product (12 g). LCMS: [M+H] 162. 1H NMR (CDCL, 500 MHz)): 7.8 (bs, 1H); 7.4 (d, 1H, J=XHz); 6.3-6.1 (m, 3H); 3.85 (s, 3H); 2.4 (s, 3H).

The compounds of this invention can be made, with modification where appropriate, in accordance with Schemes 1-4. Examples 1-97, with modification where appropriate are also produced in accordance with Schemes 1-4.

Methods of Synthesis

Compounds of the present invention can be prepared according to the following methods. The substituents are the same as in Formula I except where defined otherwise or otherwise apparent in context to one in the art. Several methods for preparing the compounds of this invention are illustrated in the following schemes and Examples. Starting materials are made from known procedures, as illustrated in the schemes or for specific Examples.

SCHEME 1

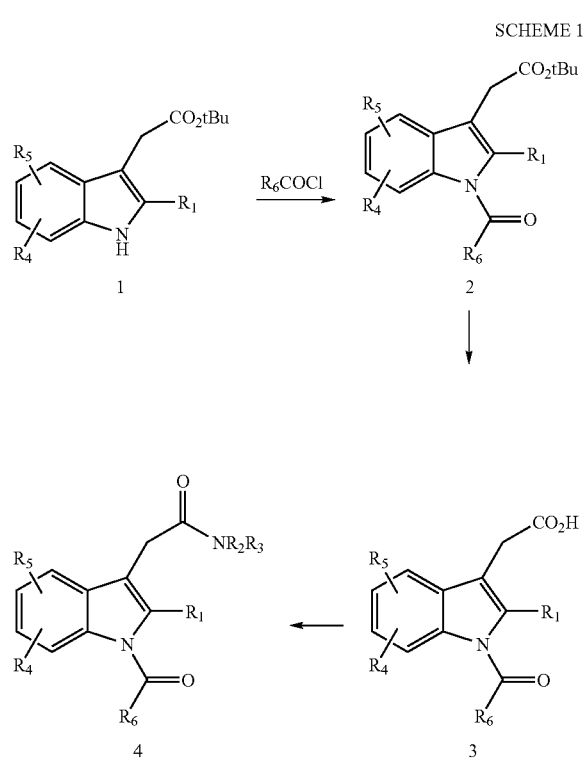

In one protocol, the compounds of the present invention are prepared as described in Reaction Scheme 1. The acid precursor of t-butyl ester 1, prepared as described by E. Shaw (J. Am. Chem. Soc., 1955, 77, 4319) is converted to compounds 2, 3, and 4 as described by T. Y. Shen et. al. (J. Am. Chem. Soc., 1963, 85, 488). Reaction of ester 1 with acid halide reagents under standard acylation conditions, gives amide derivative 2. Hydrolysis of compound 2 to acid 3 can be difficult due the acid and base-sensitivity of the amide group.

Conversion of acid 3 to amide derivatives 4 can be carried out be any number of standard protocols. In particular, three methods were used to prepare compounds of this invention. In one protocol, acid 3 in a solvent such as dichloromethane is reacted under anhydrous conditions with DCC (dicyclohexylcarbodiimide), with a base such as diisopropylethylamine, followed by the addition of amine $NHR_2R_3$. In a second protocol, amine $NHR_2R_3$ in an aprotic solvent such as acetonitrile is reacted sequentially with triethylamine, PyBroP (Bromo-tris-pyrrolidinophosphonium hexafluorophosphate) and acid 3 to give amide 4. Sometimes, this reaction mixture requires heating at reflux to achieve optimal conversion. In a third protocol, acid 3 in dichloromethane is reacted with TBTU (o-benzotriazol-1-yl-N,N,N',N',-tetramethyluronium tetrafluoroborate), amine $NHR_2R_3$ and diisopropylethyl amine to give amide 4.

SCHEME 2

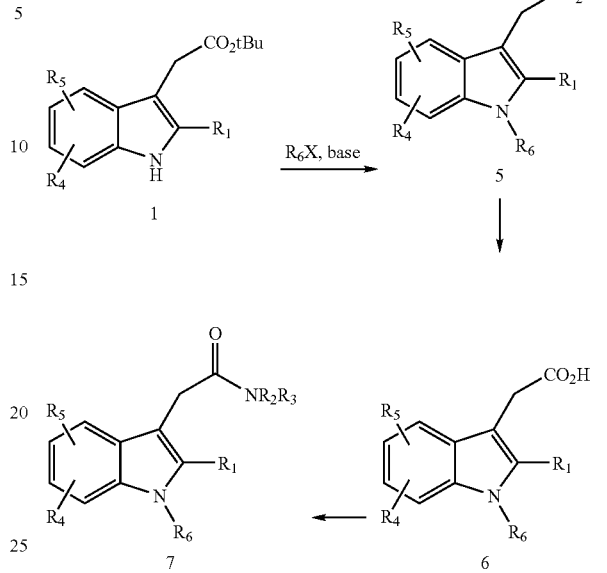

In reaction scheme 2, the indole nitrogen of t-butyl ester 1 can be alkylated with a suitable halide, triflate, ethanesulfonate, p-toluenesulfonate, etc. carried out under standard alkylation conditions to give N-alkylated derivative 5. Since this compound is no longer acid or base-sensitive, the t-butyl ester can be hydrolyzed under more standard conditions such as with TFA (trifluoroacetic acid) in a solvent such as dichloromethane to give acid 6, which in turn, can be converted to amide 7 as described in Reaction Scheme 1.

SCHEME 3

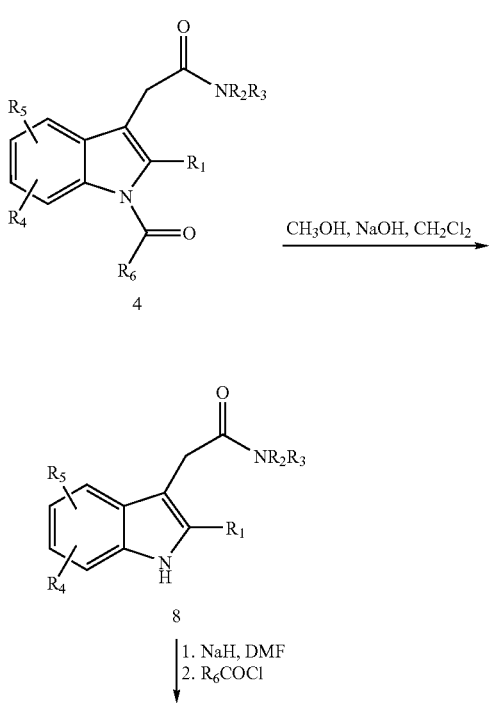

-continued

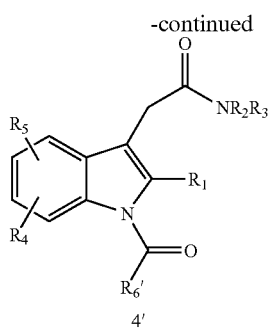
4'

In Reaction Scheme 3 describes an alternate protocol to prepare amides at the indole nitrogen. Compound 4 is hydrolyzed in a protic solvent such as methanol with a base such as NaOH at room temperature to give product 8. The indole NH group is deprotonated with sodium hydride in a solvent such as dimethylformamide (DMF). Addition of acid chloride $R_6'COCl$ gives amide derivatives 4'.

SCHEME 4

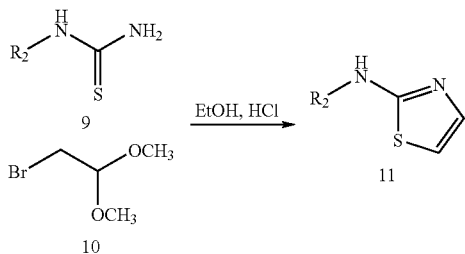

Reaction Scheme 4 describes a protocol to prepare substituted thiazole amine intermediates 11. To a suspension of an N-alkylthiourea 9 in ethanol is added 1,1-dimethoxy-2-bromoethane and concentrated HCl. The reaction mixture is heated at reflux to give substituted thiazole amine 11. Most other amine intermediates $R_1R_2NH$ were comercially available or were prepared as described in this reaction scheme. Specific variations of this will be described in the Examples.

EXAMPLE 1

N-Cyclohexyl-N-thiazol-2-yl-1-(4-chlorobenzoyl)-5-methoxy-2-methylindole-3-acetamide Step A: 1-(4-chlorobenzoyl)-5-methoxy-2-methylindole-3-acetic acid The title compound was prepared as described by Shen et. al. in J. Am. Chem. Soc., 85, 488-489 (1963).

Step B: N-Cyclohexyl-N-thiazol-2-yl amine

To a suspension of 5 g (0.032 mol) of N-cyclohexyl thiourea in 50 mL of ethanol at rt was added 5.38 g (0.0318 mol) of 1,1-dimethoxy-2-bromoethane. To the reaction mixture was then added 1.25 mL of 12N HCl and the reaction mixture was heated at reflux for 12 h. The reaction mixture was then concentrated to provide an orange-brown oil which was dissolved in 50 mL of dichloromethane. The organic solution was washed twice with 1N NaOH solution (50 mL) and then with $H_2O$. The organic fraction was dried ($Na_2SO_4$), filtered and the filtrate was concentrated to give 5.95 g of off-white solid. The residue was purified by chromatography (silica, 0 to 5% EtOAc in cyclohexane) to give the title compound. $^1H$ NMR (CDCl$_3$) δ 6.45 (1H, d), 5.69 (1H, d), 4.20-4.10 (1H, m), 1.99-1.55 (6H, 3 sets of m).

Step C: N-Cyclohexyl-N-thiazol-2-yl-1-(4-chlorobenzoyl)-5-methoxy-2-methylindole-3-acetamide To a suspension of 2 g (0.02 mol) of N-Cyclohexyl-N-thiazol-2-yl amine in 20 mL of acetonitrile at rt was added 6.1 mL (0.044 mol) of triethylamine and 10.24 g (0.022 mol) of PyBroP [bromo-tris-pyrrolidino-phosphonium hexafluorophosphate (Aldrich or NovaBiochem)]. To the reaction mixture was then added 3.93 g (0.01 mol) of 1-(4-chlorobenzoyl)-5-methoxy-2-methylindole-3-acetic acid and the reaction mixture was heated at 100° C. for 4 h. The reaction mixture was then cooled to 0° C. and the white precipitate was isolated by filtration. The filtrate was concentrated to ~10 mL, recooled to 0° C., refiltered and the filtrate was concentrated to an oil. The residue was dissolved in 100 mL of dichloromethane and the solution was washed twice with 1N HCl, and once with 1N NaHCO$_3$ solution. The organic phase was dried (Na$_2$SO$_4$) filtered and the filtrate was concentrated. The residue was purified by chromatography (silica, 0-50% EtOAc in heptane) to give the title compound. $^1H$ NMR (CDCl$_3$) δ 7.74 (1H, d), 7.66 (2H, d), 7.50 (2H, d), 7.40 (1H, d), 6.95 (1H, bs), 6.82 (1H, d), 6.67 (1H, dd), 4.59 (1H, bt), 3.84 (3H, s), 3.61 (2H, s), 2.22 (3H, s), 0.9-2.0 (10H, m)

Mass Spectrum m/e 522/524 (M+1).

EXAMPLE 2

EXAMPLE 1

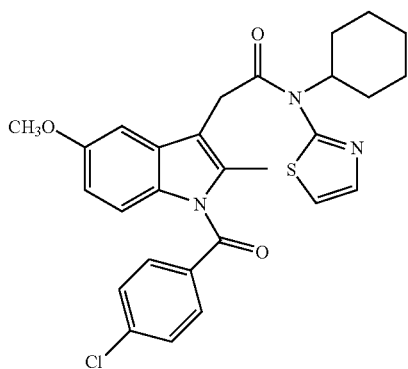

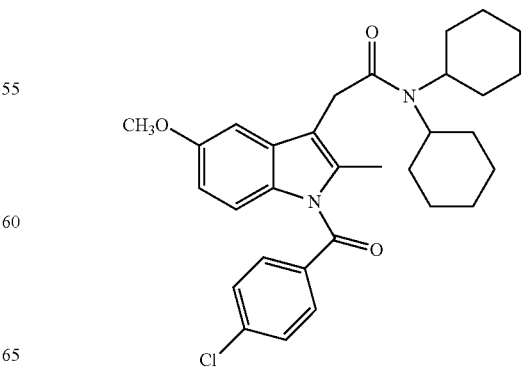

N,N-Bis-Cyclohexyl-1-(4-chlorobenzoyl)-5-methoxy-2-methylindole-3-acetamide

Into a flask was added 0.180 g (0.5 mmol) of 1-(4-chlorobenzoyl)-5-methoxy-2-methylindole-3-acetic acid, 1.8 mL of anhydrous dichloromethane, 0.194 g (0.6 mmol) of TBTU (o-benzotriazol-1-yl-N,N,N',N',-tetramethyluronium tetrafluoroborate), 0.066 mL (0.6 mmol) of dicyclohexylamine and finally 0.22 mL (1.26 mmol) of diisopropylethyl amine. The reaction was stirred at room temperature for 20 hr then diluted with more dichloromethane (10 mL). The solution was washed with dilute aqueous citric acid (2×10 mL), aqueous sodium bicarbonate (10 mL) and water (10 mL) before drying (MgSO$_4$), filtering and evaporating the filtrate. The residue was slurried with a hexanes/ethyl acetate mix to give the title compound. $^1$H NMR (CDCl$_3$) δ 7.56 (2H, d), 7.40 (2H, d), 7.01 (1H, bs), 6.61 (1H, d), 6.56 (1H, dd), 3.75 (3H, s), 3.63 (2H, s), 3.41 (1H, m), 2.73 (1H, b), 2.38 (3H, s), 0.9-1.8 (20H, m) Mass Spectrum m/e 521/523 (M+1).

The following Examples 3 to 56 were prepared from 1-(4-chlorobenzoyl)-5-methoxy-2-methylindole-3-acetic acid according to procedures described in Example 2. When Examples required alternate amide coupling conditions, the procedures are described.

EXAMPLE 3

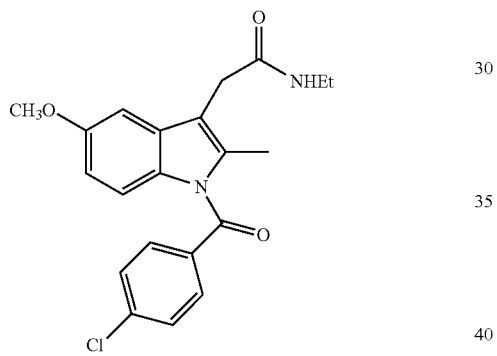

N-Ethyl-1-(4-Chlorobenzoyl)-5-methoxy-2-methylindole-3-acetamide

Mass Spectrum m/e 385/387 (M+1).

EXAMPLE 4

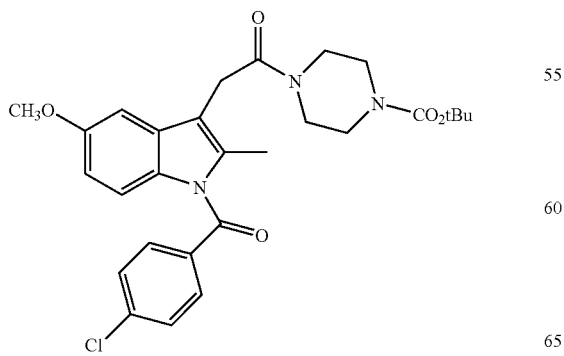

N-(4-t-butoxycarbonylpiperizin-1-yl)-1-(4-chlorobenzoyl)-5-methoxy-2-methylindole-3-acetamide Mass Spectrum m/e 426/428 (M—CO$_2$, isobutylene, +H), 470/472 (M-isobutylene +H), 526/528 (M+1).

EXAMPLE 5

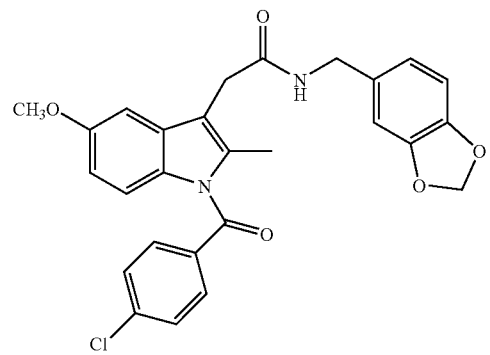

N-(3,4-Methylenedioxybenzyl)-1-(4-chlorobenzoyl)-5-methoxy-2-methylindole-3-acetamide Mass Spectrum m/e 491/493 (M+1).

EXAMPLE 6

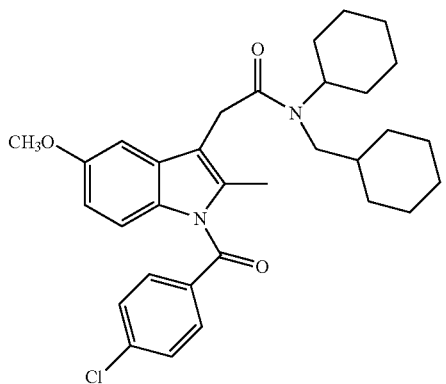

N-Cyclohexyl-N-cyclohexylmethyl-1-(4-chlorobenzoyl)-5-methoxy-2-methylindole-3-acetamide Mass Spectrum m/e 535/537 (M+1).

EXAMPLE 7

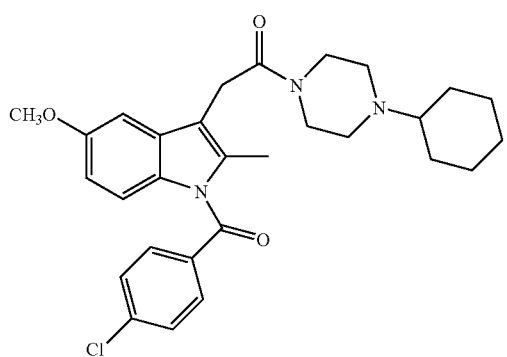

N-(4-Cyclohexylpiperazin-1-yl)-1-(4-chlorobenzoyl)-5-methoxy-2-methylindole-3-acetamide Step A: N-(piperazin-1-yl)-1-(4-chlorobenzoyl)-5-methoxy-2-methylindole-3-acetamide To a solution of 0.300 g (0.57 mmol) of N-(4-t-butoxycarbonylpiperazin-1-yl)-1-(4-chlorobenzoyl)-5-methoxy-2-methylindole-3-acetamide in 8 mL of anhydrous dichloromethane was added 1.7 mL of trifluoroacetic acid (TFA). The reaction was stirred at room temperature for 1.75 hr then evaporated to dryness, diluted with more dichloromethane (20 mL) and re-evaporated. Residual TFA was removed with a sodium carbonate wash to give the title compound. $^1$H NMR (CDCl$_3$) δ 7.58 (2H, d), 7.41 (2H, d), 6.93 (1H, d), 6.73 (1H, d), 6.60 (1H, dd), 3.75 (3H, s), 3.64 (2H, s), 3.57 (2H, m), 3.42 (2H, m), 2.75 (2H, m), 2.67 (2H, m), 2.32 (3H, s). Mass Spectrum m/e 426/428 (M+1).

Step B: N-(4-Cyclohexylpiperazin-1-yl)-1-(4-chlorobenzoyl)-5-methoxy-2-methylindole-3-acetamide To a solution of 0.112 g (0.26 mmol) of N-(piperazin-1-yl)-1-(4-chlorobenzoyl)-5-methoxy-2-methylindole-3-acetamide and 0.03 mL (0.25 mmol) of cyclohexanone in 2 mL of anhydrous tetrahydrofuran was added 0.02 mL (0.32 mmol) of acetic acid then 0.078 g (0.37 mmol) of sodium triacetoxyborohydride. The reaction was stirred at room temperature for 20 hr then partitioned between ethyl acetate (20 mL) and saturated sodium bicarbonate (20 mL). The organic phase was washed with more bicarbonate (2×20 mL) then dried (MgSO$_4$), filtered and evaporated. Preparative HPLC was used to isolate the title compound.

Mass Spectrum m/e 508/510 (M+1).

EXAMPLE 8

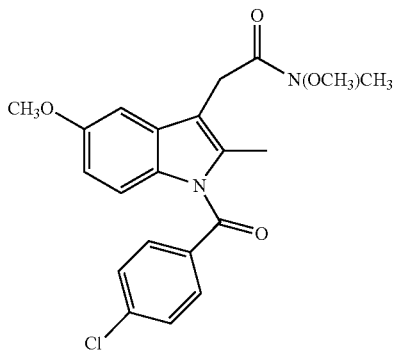

N-Methoxy-N-methyl-1-(4-chlorobenzoyl)-5-methoxy-2-methylindole-3-acetamide

Mass Spectrum m/e 401/403 (M+1).

EXAMPLE 9

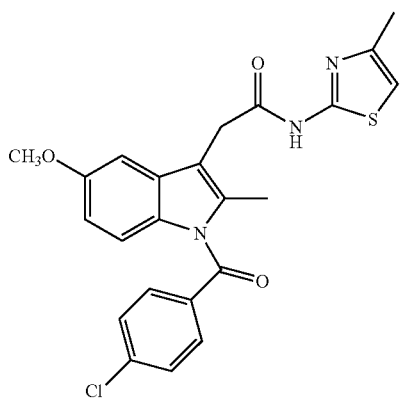

N-(4-Methylthiazol-2-yl)-1-(4-chlorobenzoyl)-5-methoxy-2-methylindole-3-acetamide Mass Spectrum m/e 454/456 (M+1).

EXAMPLE 10

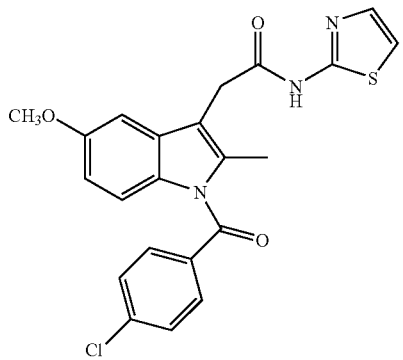

N-Thiazol-2-yl-1-(4-chlorobenzoyl)-5-methoxy-2-methylindole-3-acetamide

Mass Spectrum m/e 440/442 (M+1).

EXAMPLE 11

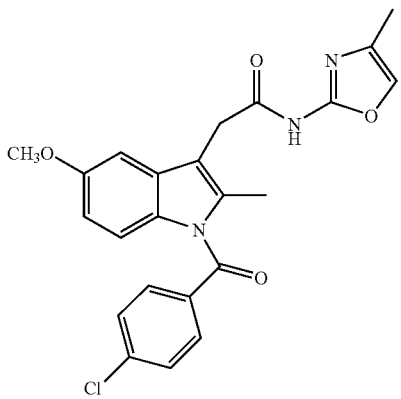

N-(4-Methyloxazol-2-yl-1-(4-chlorobenzoyl)-5-methoxy-2-methylindole-3-acetamide

Mass Spectrum m/e 438/440 (M+1).

EXAMPLE 12

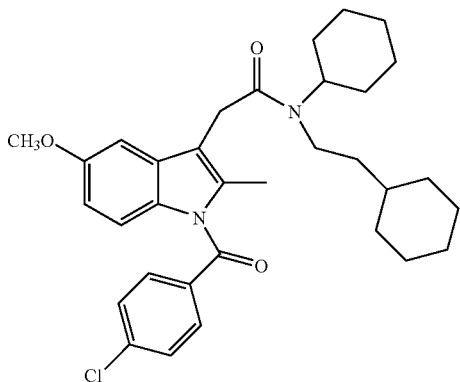

N-Cyclohexyl-N-cyclohexylmethyl-1-(4-chlorobenzoyl)-5-methoxy-2-methylindole-3-acetamide Mass Spectrum m/e 549/551 (M+1).

EXAMPLE 13

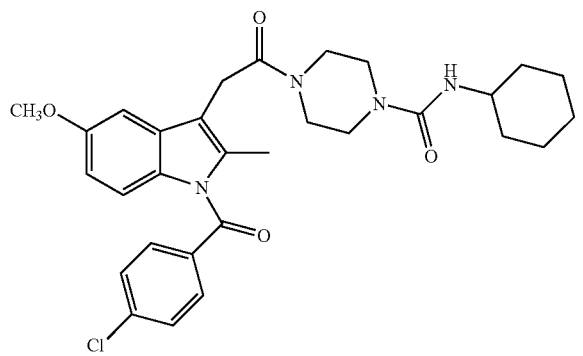

N-(4-Cyclohexylaminocarbonylpiperazin-1-yl)-1-(4-chlorobenzoyl)-5-methoxy-2-methylindole-3-acetamide Prepared as described in Example 26
Mass Spectrum m/e 551/553 (M+1).

EXAMPLE 14

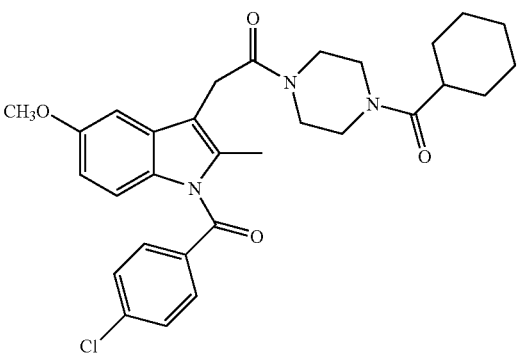

N-(4-Cyclohexylcarbonylpiperazin-1-yl)-1-(4-chlorobenzoyl)-5-methoxy-2-methylindole-3-acetamide Prepared as described in Example 26
Mass Spectrum m/e 536/538 (M+1).

EXAMPLE 15

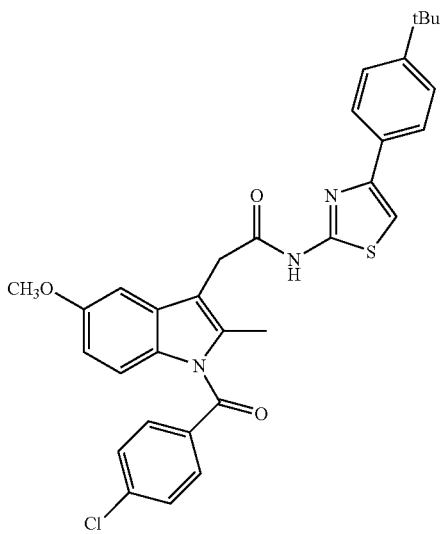

N-(4-(4-t-Butylphenyl)thiazol-2-yl)-1-(4-chlorobenzoyl)-5-methoxy-2-methylindole-3-acetamide Mass Spectrum m/e 572/574 (M+1).

EXAMPLE 16

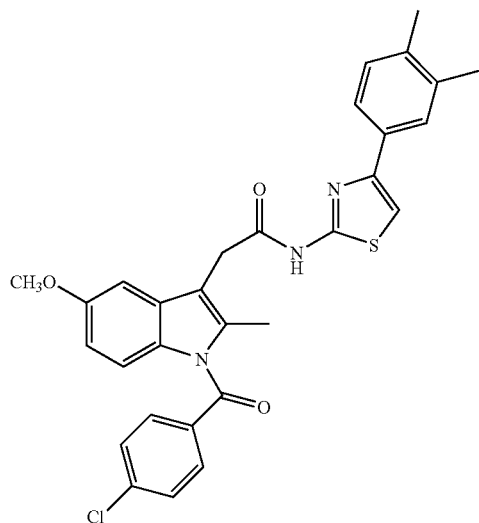

N-(4-(3,4-Dimethyl)phenylthiazol-2-yl)-1-(4-chlorobenzoyl)-5-methoxy-2-methylindole-3-acetamide Mass Spectrum m/e 544/546 (M+1).

EXAMPLE 17

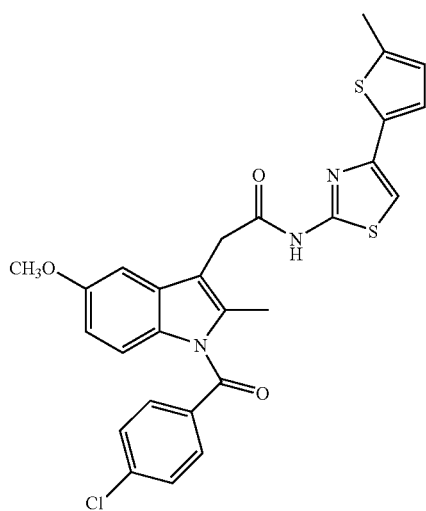

N-(4-(5-Methylthiophen-2-yl)thiazol-2-yl)-1-(4-chlorobenzoyl)-5-methoxy-2-methylindole-3-acetamide Mass Spectrum m/e 536/538 (M+1).

EXAMPLE 18

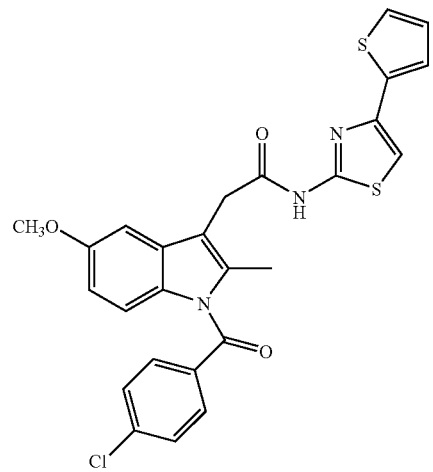

N-(4-(Thiophen-2-yl)thiazol-2-yl)-1-(4-chlorobenzoyl)-5-methoxy-2-methylindole-3-acetamide Mass Spectrum m/e 522/524 (M+1).

EXAMPLE 19

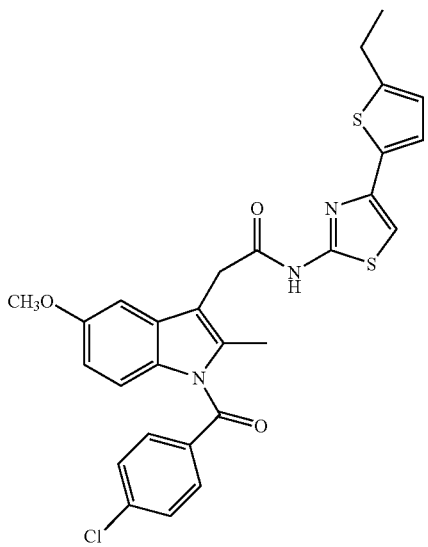

N-(4-(5-Ethylthiophen-2-yl)thiazol-2-yl)-1-(4-chlorobenzoyl)-5-methoxy-2-methylindole-3-acetamide Mass Spectrum m/e 550/552 (M+1).

EXAMPLE 20

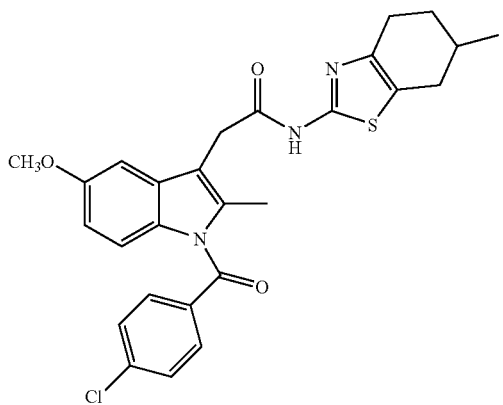

N-(6-methyltetrahydrobenzthiazol-2-yl)-1-(4-chlorobenzoyl)-5-methoxy-2-methylindole-3-acetamide Mass Spectrum m/e 508/510 (M+1).

EXAMPLE 21

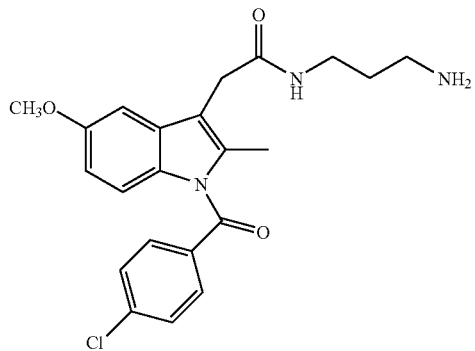

N-(3-Aminoprop-1-yl)-1-(4-chlorobenzoyl)-5-methoxy-2-methylindole-3-acetamide

Prepared as described in Example 7 Part A
Mass Spectrum m/e 414/416 (M+1).

EXAMPLE 22

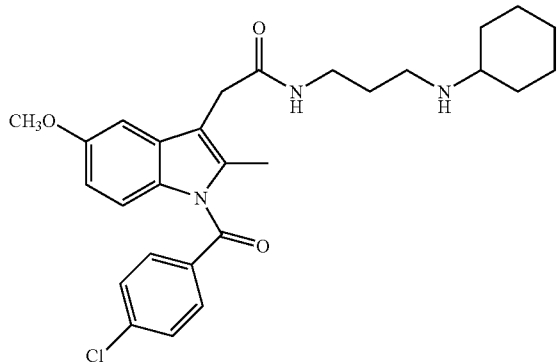

N-(3-Cyclohexylaminoprop-1-yl)-1-(4chlorobenzoyl)-5-methoxy-2-methylindole-3-acetamide Prepared as described in Example 7
Mass Spectrum m/e 496/498 (M+1).

EXAMPLE 23

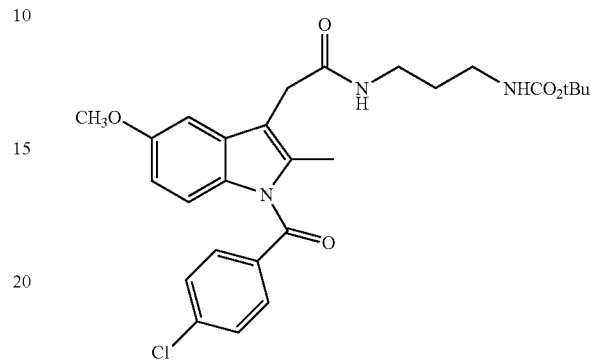

N-(3-t-Butoxycarbonylaminoprop-1-yl)-1-(4-chlorobenzoyl)-5-methoxy-2-methylindole-3-acetamide Mass Spectrum m/e 514/516 (M+1).

EXAMPLE 24

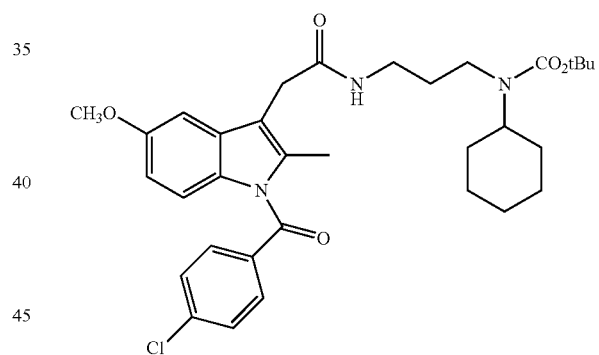

N-(3-t-Butoxycarbonyl-3-cyclohexylaminoprop-1-yl)-1-(4-chlorobenzoyl)-5-methoxy-2-methylindole-3-acetamide To a suspension of 0.100 g (0.2 mmol) of N-(3-cyclohexylaminoprop-1-yl)-1-(4-chlorobenzoyl)-5-methoxy-2-methylindole-3-acetamide (Example 22) in 1 mL of acetonitrile was added 0.003 g (0.02 mmol) of 4-(dimethylamino)pyridine followed by 0.048 g (0.22 mmol) of di(t-butyl) dicarbonate and the reaction stirred at room temperature for 48 hr. Ethyl acetate (1 mL) was added followed by 10% citric acid (2 mL). The layers were separated and the organic phase dried ($Na_2SO_4$). After filtering and evaporating the residue, column chromatography gave the title compound. $^1$H NMR ($CDCl_3$) δ 7.60 (2H, d), 7.38 (2H, bd), 6.85 (2H, m), 6.61 (1H, bd), 3.74 (3H, s), 3.55 (2H, s), 3.33 (1H, m), 3.09 (2H, m), 2.96 (2H, m), 2.32 (3H, s), 0.9-1.8 (21H, m).

Mass Spectrum m/e 596/598 (M+1).

EXAMPLE 25

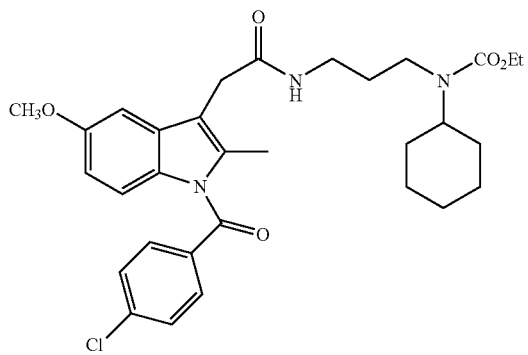

N-(3-Ethoxycarbonyl-3-cyclohexylaminoprop-1-yl)-1-(4-chlorobenzoyl)-5-methoxy-2-methylindole-3-acetamide Prepared as described in Example 26
Mass Spectrum m/e 568/570 (M+1).

EXAMPLE 26

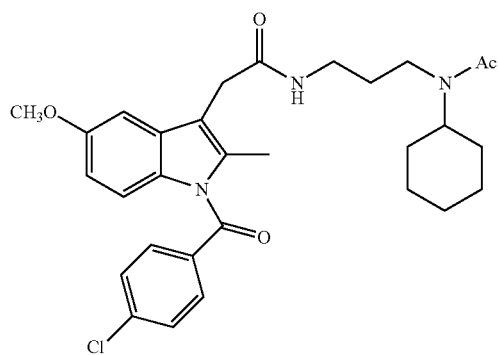

N-(3-Acetyl-3-cyclohexylaminoprop-1-yl)-1-(4-chlorobenzoyl)-5-methoxy-2-methylindole-3-acetamide To a solution of 0.100 g (0.2 mmol) of N-(3-cyclohexylaminoprop-1-yl)-1-(4-chlorobenzoyl)-5-methoxy-2-methylindole-3-acetamide in 1 mL of anhydrous dichloromethane was added 0.04 mL (0.24 mmol) of diisopropylethyl amine followed by 0.015 mL (0.2 mmol) of acetyl chloride. The reaction was stirred at room temperature for 20 hr then diluted with more dichloromethane (2 mL). The solution was washed with dilute aqueous citric acid (1 mL) before drying ($Na_2SO_4$), filtering and evaporating. The residue was purified by preparative HPLC to give the title compound. $^1$H NMR ($CDCl_3$) δ 7.68 (2H, d), 7.39 (2H, d), 7.16 (1H, bt), 6.86 (1H, d), 6.79 (1H, d), 6.61 (1H, dd), 3.75 (3H, s), 3.57 (2H, s), 3.36 (1H, bt), 3.06 (4H, m), 2.33 (3H, s), 1.96 (3H, s), 0.9-1.8 (12H, m).

Mass Spectrum m/e 538/540 (M+1).

EXAMPLE 27

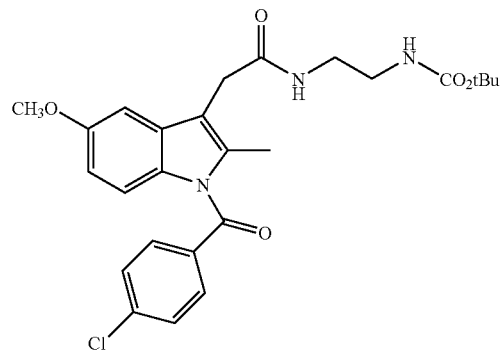

N-(2-t-Butoxycarbonylaminoeth-1-yl)-1-(4-chlorobenzoyl)-5-methoxy-2-methylindole-3-acetamide Mass Spectrum m/e 500/502 (M+1).

EXAMPLE 28

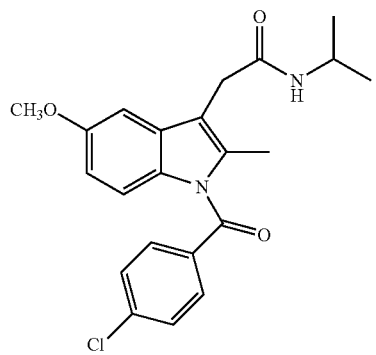

N-Isopropyl-1-(4-chlorobenzoyl)-5-methoxy-2-methylindole-3-acetamide

Mass Spectrum m/e 399/401 (M+1).

EXAMPLE 29

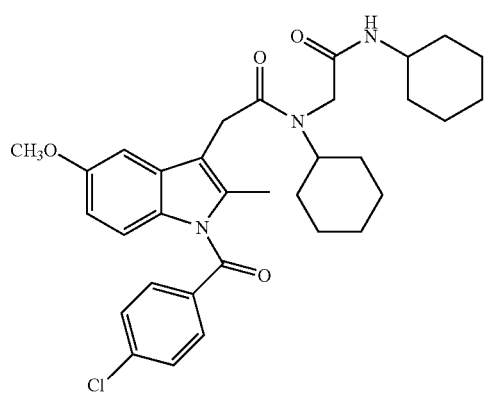

N-(Cyclohexyl-N-cyclohexylaminocarbonylmethyl)-1-(4-chlorobenzoyl)-5-methoxy-2-methylindole-3-acetamide Step A: N-Cyclohexyl-2-cyclohexylamino-acetamide A solution of 1.5 mL (18.8 mmol) of chloroacetyl chloride in 30 mL of anhydrous dichloromethane was cooled to 0° C. before adding 6.56 mL (47.1 mmol) of triethylamine and 4.74 mL (41.1 mmol) of cyclohexylamine. The reaction stirred for 24 hr at room temperature then 0.5 g (4.7 mmol) of 4-(dimethylamino)pyridine was added and stirring continued for a further 48 hr. The reaction was diluted with dichloromethane (30 mL) and washed with dilute citric acid (2×30 mL), saturated sodium bicarbonate (30 mL) and brine (30 mL) before drying ($Na_2SO_4$), filtering and evaporating to give the title compound.

Mass Spectrum m/e 239 (M+1).

Step B: Prepared as described in Example 2

Mass Spectrum m/e 478/480 (M-$CO_2$, isobutylene +H); 578/580 (M+1).

EXAMPLE 30

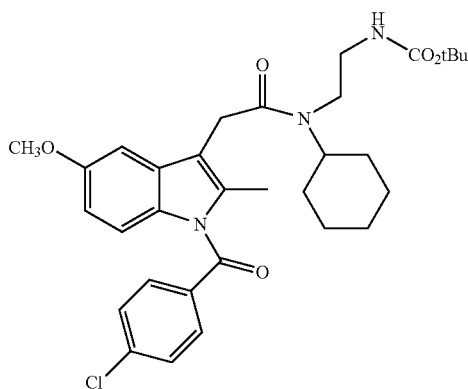

N-Cyclohexyl-N-(2-t-butylcarbonylaminoeth-1-yl)-1-(4-chlorobenzoyl)-5-methoxy-2-methylindole-3-acetamide Step A: 1-(4-chlorobenzoyl)-5-methoxy-2-methylindole-3-acetyl chloride A suspension of 1.0 g (2.79 mmol) of 1-(4-Chlorobenzoyl)-5-methoxy-2-methylindole-3-acetic acid in 10 mL of anhydrous dichloromethane was cooled on ice before adding 0.51 mL (5.86 mmol) of oxalyl chloride followed by a drop of dimethyl formamide. The reaction was stirred at room temperature for 20 hr then evaporated to dryness to leave the title compound.

Mass Spectrum m/e 243 (M+1).

Step B: N-Cyclohexyl-N-(2-t-butoxycarbonylaminoeth-1-yl)amine

To a solution of 1.04 mL (1.0 mmol) of cyclohexanone and 1.6 g (1.0 mmol) of N-(2-t-butoxycarbonylaminoeth-1-yl)amine in 24 mL of tetrahydrofuran were added 0.71 mL (1.2 mmol) of acetic acid and 2.97 g (1.4 mmol) of sodium triacetoxyborohydride. The reaction stirred at room temperature for 20 hr then saturated sodium bicarbonate (12 mL) was added and the mixture extracted with ethyl acetate (12 mL). The organic phase was washed with more saturated sodium bicarbonate (12 mL) and brine (12 mL). At this point a crystalline precipitate formed which was filtered off and washed with water and ethyl acetate to leave the title compound.

Step C: N-Cyclohexyl-N-(2-t-butylcarbonylaminoeth-1-yl)-1-(4-chlorobenzoyl)-5-methoxy-2-methylindole-3-acetamide To a stirred solution of 0.31 g (0.83 mmol) of 1-(4chlorobenzoyl)-5-methoxy-2-methylindole-3-acetyl chloride in 20 mL of toluene was added 0.2 g (0.83 mmol) of N-cyclohexyl-N-(2-t-butylcarbonylaminoeth-1-yl)amine, 0.3 mL (1.65 mmol) of diisopropylethyl amine and 0.050 g (0.42 mmol) of 4-(dimethylamino)pyridine. The reaction was heated at reflux for 48 hr before washing with 1M citric acid (20 mL), saturated sodium bicarbonate (20 mL) and brine (20 mL). The organic phase was dried ($MgSO_4$), filtered and evaporated before purifying by preparative HPLC to give the title compound. $^1$H NMR ($CDCl_3$) δ 7.67 (2H, d), 7.51 (2H, d), 7.03 (1H, bs), 6.75 (1H, d), 6.69 (1H, d), 5.16 (1H, m), 3.84 (3H, s), 3.81 (2H, s), 3.64 (1H, m), 3.39 (2H, m), 3.29 (2H, m), 2.48 (3H, s), 0.9-1.8 (19H, m).

Mass Spectrum m/e 482/484 (M-$CO_2$, isobutylene +H), 526/528 (M-isobutylene+H), 582/584 (M+1).

EXAMPLE 31

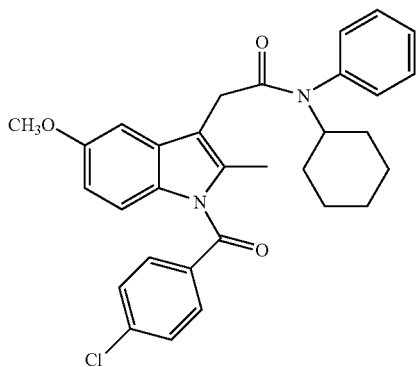

N-Cyclohexyl-N-phenyl-1-(4-chlorobenzoyl)-5-methoxy-2-methylindole-3-acetamide

Mass Spectrum m/e 515/517 (M+1).

EXAMPLE 32

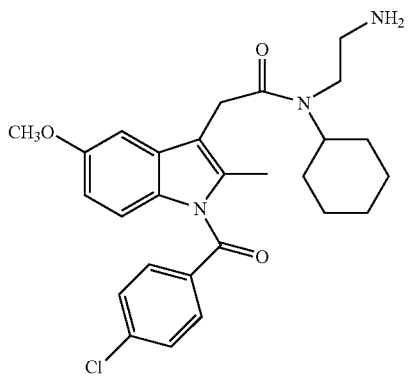

N-Cyclohexyl-N-(2-aminoeth-1-yl)-1-(4-chlorobenzoyl)-5-methoxy-2-methylindole-3-acetamide Prepared as described in Example 7 Step A.
Mass Spectrum m/e 482/484 (M+1).

EXAMPLE 33

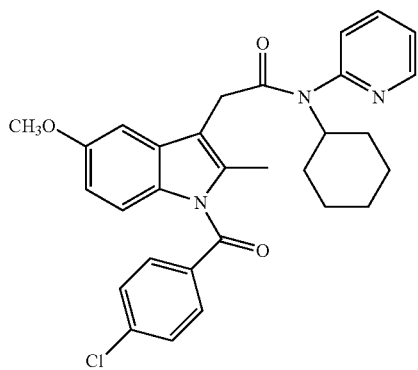

N-Cyclohexyl-N-(pyridin-2-yl)-1-(4-chlorobenzoyl)-5-methoxy-2-methylindole-3-acetamide Prepared as described in Example 30 Step C.
Mass Spectrum m/e 516/518 (M+1).

EXAMPLE 34

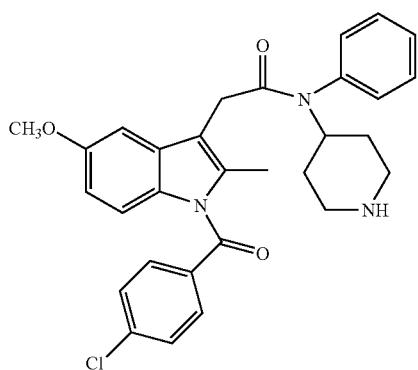

N-(Piperidin-4yl)-N-phenyl-1-(4-chlorobenzoyl)-5-methoxy-2-methylindole-3-acetamide Prepared as described in Example 30 Step C.
Mass Spectrum m/e 560/562 (M-isobutylene+H); 616/618 (M+1).

EXAMPLE 35

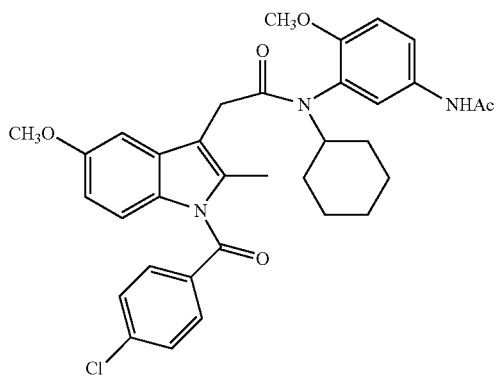

N-(Cyclohexyl)-N-(2-methoxy-5-acetylaminophenyl)-1-(4-chlorobenzoyl)-5-methoxy-2-methylindole-3-acetamide Mass Spectrum m/e 602/604 (M+1).

EXAMPLE 36

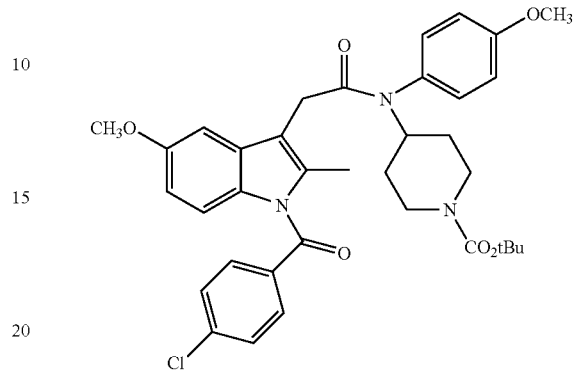

N-(t-Butoxylcarbonylpiperidin-4-yl)-N-(4-methoxyphenyl)-1-(4-chlorobenzoyl)-5-methoxy-2-methylindole-3-acetamide Prepared as described in Example 1.
Mass Spectrum m/e 590/592 (M-isobutylene+H); 646/648 (M+1).

EXAMPLE 37

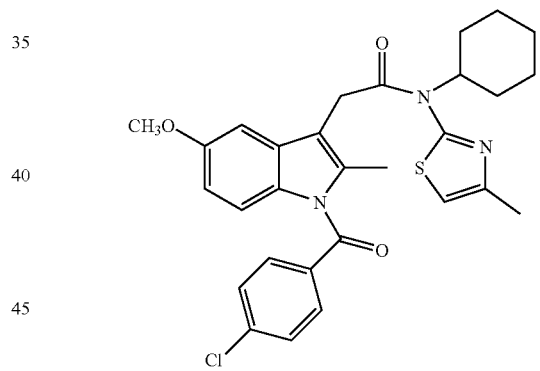

N-Cyclohexyl-N-(4-methylthiazol-2-yl)-1-(4-chlorobenzoyl)-5-methoxy-2-methylindole-3-acetamide N-cyclohexyl-N-(4-methylthiazol-2-yl)amine
To a solution of 0.85 mL (8.28 mmol) of cyclohexanone and 1.0 g (8.75 mmol) of 2-amino-4-methylthiazole in 10 mL of tetrahydrofuran was added 0.5 mL (8.75 mmol) of acetic acid and 4.64 g (21.8 mmol) of sodium triacetoxyborohydride. After stirring for 16 hr at rt, a further 0.45 mL (4.37 mmol) of cyclohexanone and 0.926 g (4.37 mmol) of sodium triacetoxyborohydride was added and stirring continued for 72 hr at rt. Ethyl acetate (15 mL) was added and the mixture washed with saturated sodium bicarbonate (2×15 mL) then dried (Na$_2$SO$_4$). Purification by chromatography on silica gave the title compound.

This was used as described in Example 30 Step C.
Mass Spectrum m/e 536/538 (M+1).

EXAMPLE 38

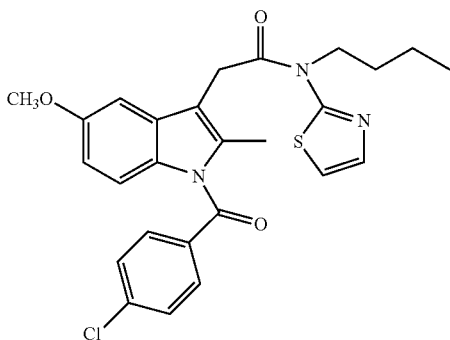

N-n-Butyl-N-(thiazol-2-yl)-1-(4-chlorobenzoyl)-5-methoxy-2-methylindole-3-acetamide Mass Spectrum m/e 496/498 (M+1).

EXAMPLE 39

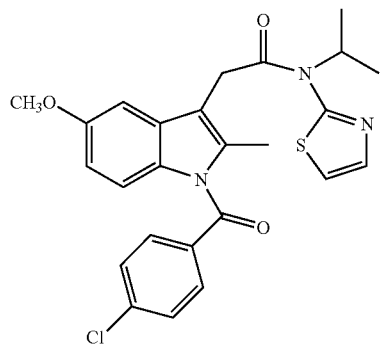

N-Isopropyl-N-(thiazol-2-yl)-1-(4-chlorobenzoyl)-5-methoxy-2-methylindole-3-acetamide Mass Spectrum m/e 482/484 (M+1).

EXAMPLE 40

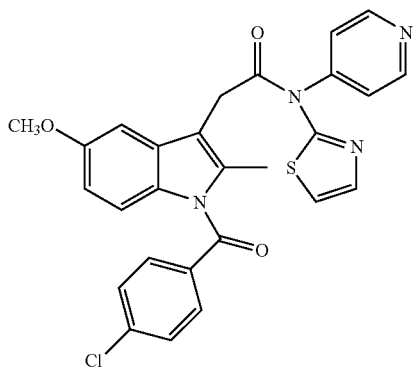

N-Pyridin-4-yl-N-(thiazol-2-yl)-1-(4-chlorobenzoyl)-5-methoxy-2-methylindole-3-acetamide Prepared as described in Example 1 Step B and in Example 2. Mass Spectrum m/e 517/519 (M+1).

EXAMPLE 41

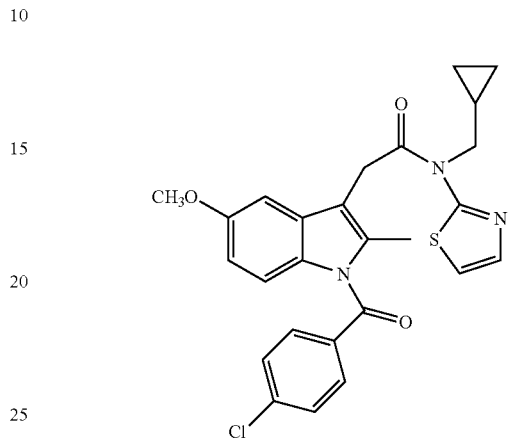

N-Cyclopropylmethyl-N-(thiazol-2-yl)-1-(4-chlorobenzoyl)-5-methoxy-2-methylindole-3-acetamide Prepared as described in Example 1 Step B and in Example 2. Mass Spectrum m/e 494/496 (M+1).

EXAMPLE 42

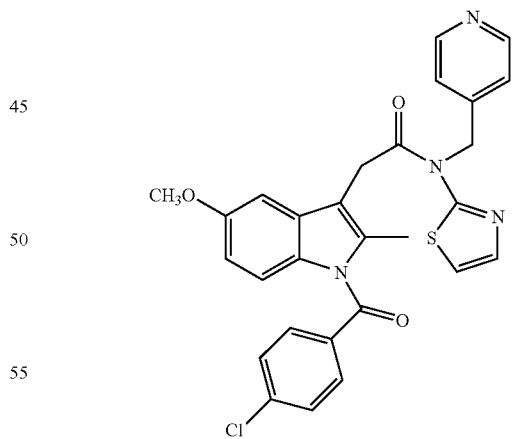

N-(Pyridin-4-ylmethyl-N-(thiazol-2-yl)-1-(4-chlorobenzoyl)-5-methoxy-2-methylindole-3-acetamide Prepared as described in Example 1 Step B and in Example 2. Mass Spectrum m/e 531/533 (M+1).

EXAMPLE 43

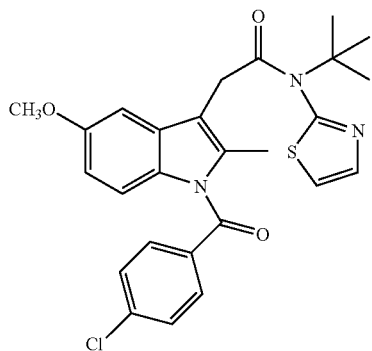

N-t-Butyl-N-(thiazol-2-yl)-1-(4-chlorobenzoyl)-5-methoxy-2-methylindole-3-acetamide Prepared as described in Example 1 Step B and Example 2. Mass Spectrum m/e 496/498 (M+1).

EXAMPLE 44

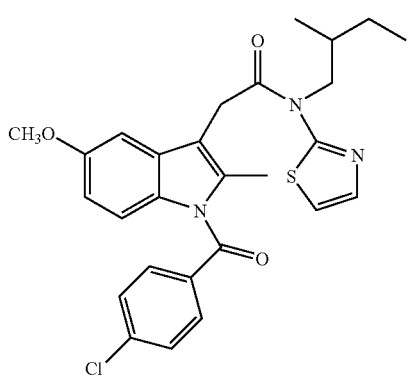

N-(n-But-2-ylmethyl)-N-(thiazol-2-yl)-1-(4-chlorobenzoyl)-5-methoxy-2-methylindole-3-acetamide Prepared as described in Example 1 Step B and in Example 2. Mass Spectrum m/e 510/512 (M+1).

EXAMPLE 45

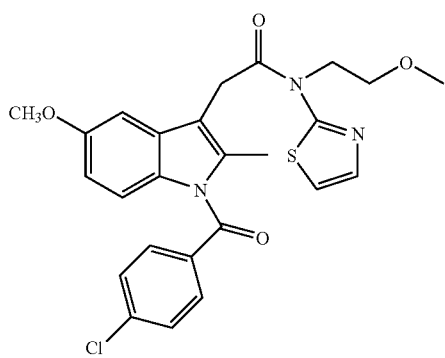

N-(2-Methoxyeth-1-yl)-N-(thiazol-2-yl)-1-(4-chlorobenzoyl)-5-methoxy-2-methylindole-3-acetamide Prepared as described in Example 1 Step B and Example 2. Mass Spectrum m/e 498/500 (M+1).

EXAMPLE 46

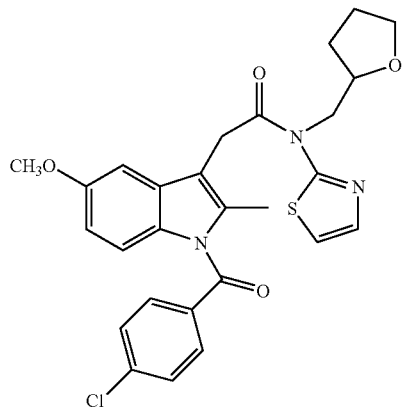

N-(2-Tetrahydrofuranylmethyl)-N-(thiazol-2-yl)-1-(4-chlorobenzoyl)-5-methoxy-2-methylindole-3-acetamide Prepared as described in Example 1 Step B and in Example 2. Mass Spectrum m/e 524/526 (M+1).

EXAMPLE 47

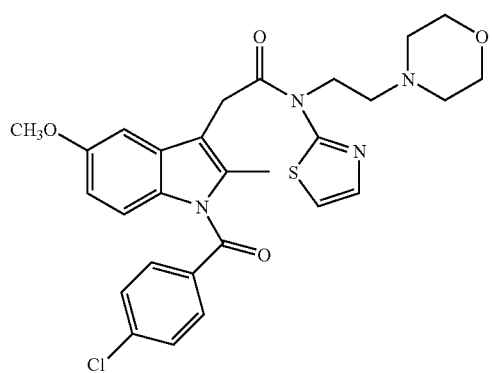

N-(2-Morpholinoeth-1-yl)-N-(thiazol-2-yl)-1-(4-chlorobenzoyl)-5-methoxy-2-methylindole-3-acetamide Prepared as described in Example 1 Step B and in Example 2. Mass Spectrum m/e 553/555 (M+1).

EXAMPLE 48

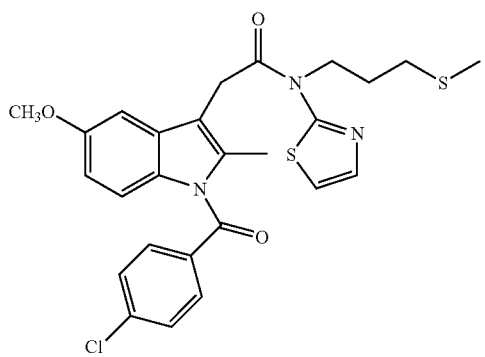

N-(3-Methylthioprop-1-yl)-N-(thiazol-2-yl)-1-(4-chlorobenzoyl)-5-methoxy-2-methylindole-3-acetamide N-(3-methylthio)prop-1-yl thiourea To 30 mL of methanol at 0° C. was added cautiously 5.9 mL (83 mmol) of acetyl chloride. After 15 min., 2.9 g (27 mmol) of 3-methylthiopropyl amine was added and the reaction stirred for 30 min. before evaporating to dryness. The residue was dissolved in 50 mL of anhydrous tetrahydrofuran and 3.9 g (40.5 mmol) of potassium thiocyanate added. The reaction was heated at reflux for 16 hr before evaporating to near dryness and diluting with water (50 mL) and 1M NaOH (5 mL). The mixture was extracted with ethyl acetate (2×100 mL) and the combined organic layers dried ($Na_2SO_4$), filtered and evaporated to give the title compound. $^1$H NMR ($CDCl_3$) δ 5.50 (3H, bs), 3.06 (2H, t), 2.59 (2H, t), 2.09 (3H, s), 1.96 (2H, quintet).

This was used as described in Example 1.
Mass Spectrum m/e 528/530 (M+1).

EXAMPLE 49

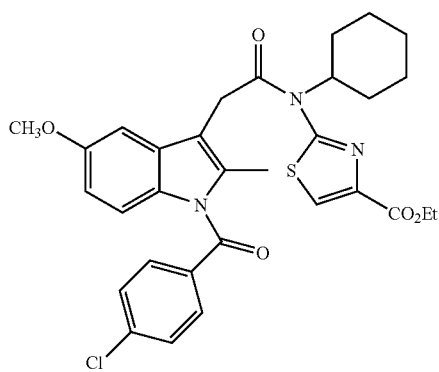

N-(Cyclohexyl)-N-(4-Ethoxycarbonylthiazol-2-yl)-1-(4-chlorobenzoyl)-5-methoxy-2-methylindole-3-acetamide N-(Cyclohexyl)-N-(4-Ethoxycarbonylthiazol-2-yl)amine To a suspension of 0.25 g (1.6 mmol) of N-cyclohexylthiourea in 2.5 mL of ethanol was added 0.31 g of ethyl bromopyruvate. The reaction was heated at reflux for 17 hr then evaporated to leave the title compound.
Mass Spectrum m/e 255 (M+1).

This was used as described in Example 1 Step C.
Mass Spectrum m/e 594/596 (M+1).

EXAMPLE 50

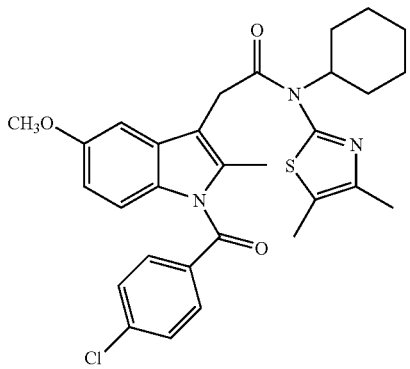

N-(Cyclohexyl)-N-(3,4-Dimethylthiazol-2-yl)-1-(4-chlorobenzoyl)-5-methoxy-2-methylindole-3-acetamide Prepared as described in Example 49 and Example 2.
Mass Spectrum m/e 550/552 (M+1).

EXAMPLE 51

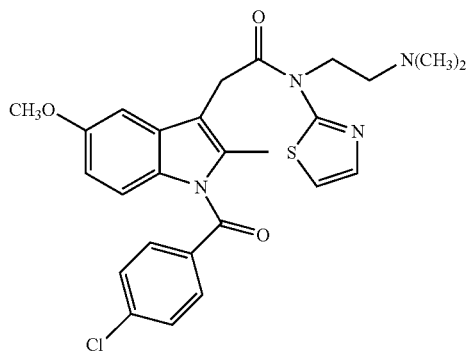

N-(2-Dimethylaminoeth-1-yl)-N-(thiazol-2-yl)-1-(4-chlorobenzoyl)-5-methoxy-2-methylindole-3-acetamide Prepared as described in Example 48 and in Example 2.
Mass Spectrum m/e 511/513 (M+1).

EXAMPLE 52

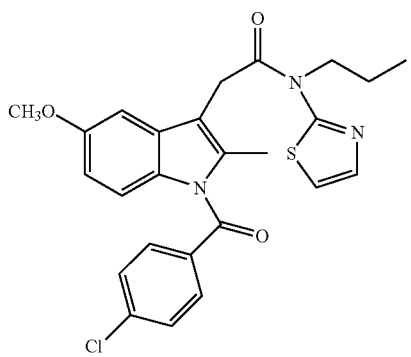

N-(n-Propyl)-N-(thiazol-2-yl)-1-(4-chlorobenzoyl)-
5-methoxy-2-methylindole-3-acetamide Prepared as described in Example 1.

Mass Spectrum m/e 482/484 (M+1).

EXAMPLE 53

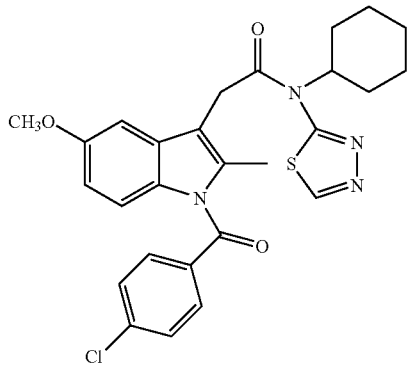

N-(Cyclohexyl)-N-(thiadiazol-2-yl)-1-(4-chloroben-
zoyl)-5-methoxy-2-methylindole-3-acetamide Step A: N-Cyclohexyl-N-thiadiazol-2-yl amine A solution of 100 mg (0.6 mmol) of N-cyclohexyl thiosemi-carbazide in 2 mL of trimethyl orthoformate was heated overnight at 80° C. then 12M HCl (2 drops) was added and reflux continued for a further 2 hr. The reaction was concentrated and the residue chromatographed on silica gel to give the title compound. $^1$H NMR (CDCl$_3$) δ 8.30 (1H, s), 5.88 (1H, s), 3.30 (1H, m), 2.06 (2H, m), 1.0-1.8 (8H, m).

Step B: As described in Example 1 Step C.

Mass Spectrum m/e 523/525 (M+1).

EXAMPLE 54

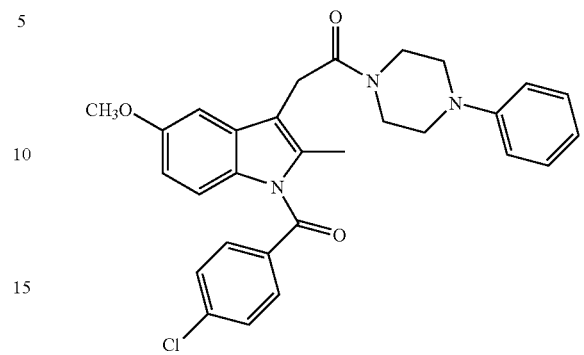

N-(4-Phenylpiperazinyl)-1-(4-chlorobenzoyl)-5-
methoxy-2-methylindole-3-acetamide Mass Spectrum m/e 502/504 (M+1).

EXAMPLE 55

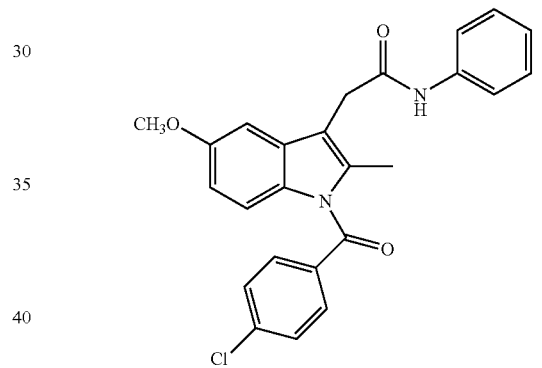

N-Phenyl-1-(4-chlorobenzoyl)-5-methoxy-2-meth-
ylindole-3-acetamide

Mass Spectrum m/e 433/435 (M+1).

EXAMPLE 56

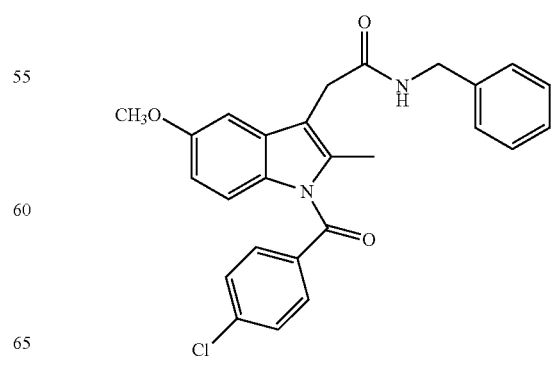

N-Benzyl-1-(4-chlorobenzoyl)-5-methoxy-2-methylindole-3-acetamide

Mass Spectrum m/e 447/449 (M+1).

EXAMPLE 57

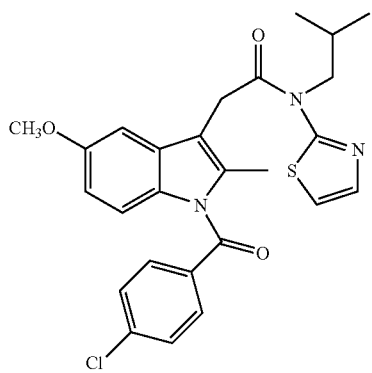

N-(isobutyl)-N-(thiazol-2-yl)-1-(4-chlorobenzoyl)-5-methoxy-2-methylindole-3-acetamide Prepared as described in Example 1 Step B and in Example 2. Mass Spectrum m/e 496/498 (M+1).

EXAMPLE 58

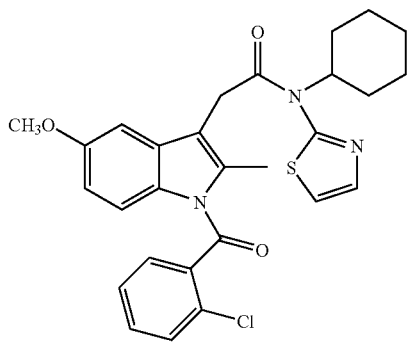

N-Cyclohexyl-N-thiazol-2-yl-1-(2-chlorobenzoyl)-5-methoxy-2-methylindole-3-acetamide Step A: N-Cyclohexyl-N-thiazol-2-yl-5-methoxy-2-methylindole-3-acetamide
A solution of 2.42 g (0.0045 mol) of N-Cyclohexyl-N-thiazol-2-yl-1-(4-chlorobenzoyl)-5-methoxy-2-methylindole-3-acetamide in 2.4 mL of dichloromethane, 48 mL of methanol and 24 mL of 1N aqueous NaOH solution was stirred at rt for 90 min. During this time, the title compound formed as a precipitate. It was filtered, washed with water and dried.

Step B: N-Cyclohexyl-N-thiazol-2-yl-1-5-methoxy-2-methylindole-3-acetamide
To a mixture of 0.006 g (0.00055 mol) of sodium hydride (60%, washed with hexanes) in 2 mL of DMF at 0° C. was added a solution of 0.05 g (0.00013 mol) of N-Cyclohexyl-N-thiazol-2-yl-1-(2-chlorobenzoyl)-5-methoxy-2-methylindole-3-acetamide in 2 mL of DMF and the reaction mixture was stirred at 0° C. for 20 min. To this mixture was added 0.02 mL 0.00017 mol) of 2-chlorobenzoyl chloride. After stirring for 18 h, to the reaction mixture was added 5 mL of H$_2$O. The mixture was extracted with ethyl acetate (3×10 mL). The organic fractions were dried (Na$_2$SO$_4$), filtered and the filtrate was concentrated. The residue was purified by chromatography (silica, 30% EtOAc:heptane) to give the title compound.
$^1$H NMR (CDCl$_3$) δ: 7.63(1H); 7.5-7.2(5H); 7.07(1H); 6.83 (1H); 6.59(1H); 4.47(1H); 3.77(3H); 3.49(2H); 1.98(3H) 1.78(2H); 1.67(2H); 1.51(1H) 1.4-1.1(4H); 0.90(1H). Mass Spectrum m/e 522/524 (M+1).

The following Examples 59 to 80 were prepared from N-Cyclohexyl-N-thiazol-2-yl-5-methoxy-2-methylindole-3-acetamide according to procedures described in Example 58.

EXAMPLE 59

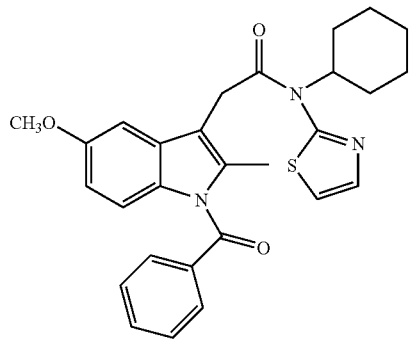

N-Cyclohexyl-N-thiazol-2-yl-1-(benzoyl)-5-methoxy-2-methylindole-3-acetamide

Mass Spectrum m/e 488 (M+1).

EXAMPLE 60

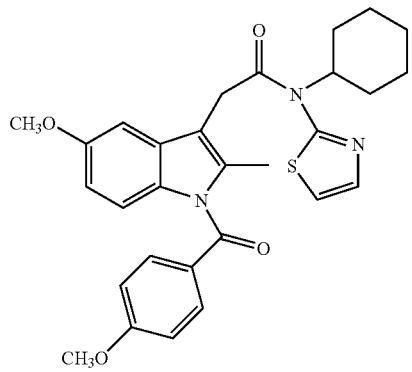

N-Cyclohexyl-N-thiazol-2-yl-1-(4-methoxybenzoyl)-5-methoxy-2-methylindole-3-acetamide Mass Spectrum m/e 518 (M+1).

EXAMPLE 61

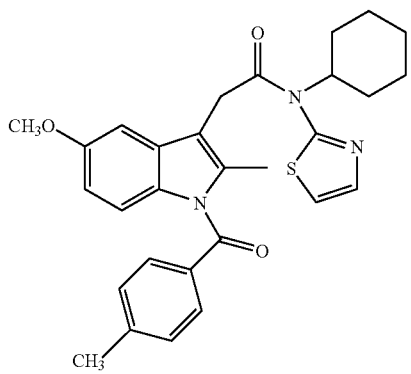

N-Cyclohexyl-N-thiazol-2-yl-1-(4-methylbenzoyl)-5-methoxy-2-methylindole-3-acetamide Mass Spectrum m/e 502 (M+1).

EXAMPLE 62

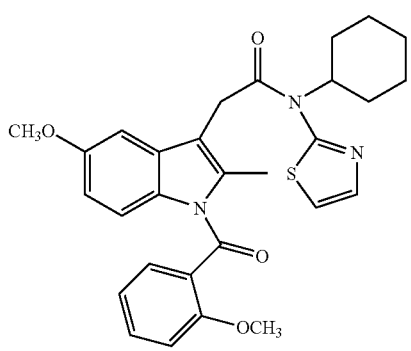

N-Cyclohexyl-N-thiazol-2-yl-1-(2-methoxybenzoyl)-5-methoxy-2-methylindole-3-acetamide Mass Spectrum m/e 518 (M+1).

EXAMPLE 63

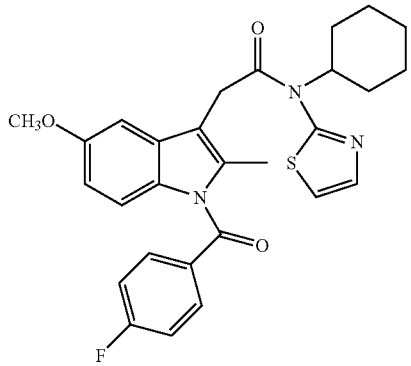

N-Cyclohexyl-N-thiazol-2-yl-1-(4-fluorobenzoyl)-5-methoxy-2-methylindole-3-acetamide Mass Spectrum m/e 506 (M+1).

EXAMPLE 64

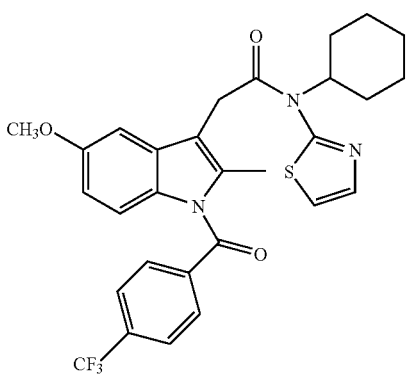

N-Cyclohexyl-N-thiazol-2-yl-1-(4-trifluoromethylbenzoyl)-5-methoxy-2-methylindole-3-acetamide Mass Spectrum m/e 556 (M+1).

EXAMPLE 65

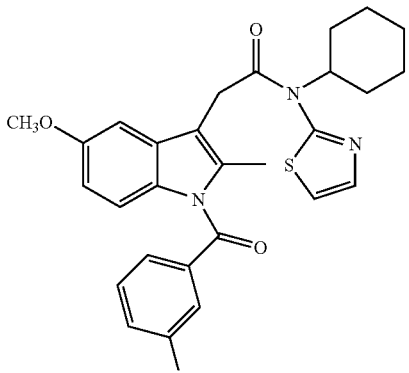

N-Cyclohexyl-N-thiazol-2-yl-1-(3-methoxybenzoyl)-5-methoxy-2-methylindole-3-acetamide Mass Spectrum m/e 518 (M+1).

EXAMPLE 66

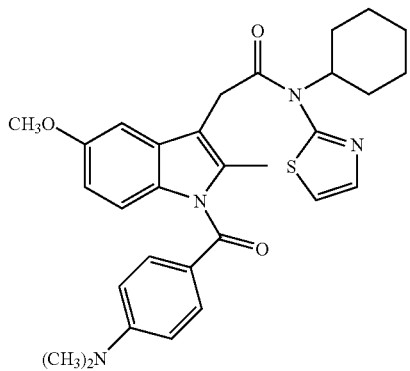

N-Cyclohexyl-N-thiazol-2-yl-1-(4-dimethylaminobenzoyl)-5-methoxy-2-methylindole-3-acetamide Mass Spectrum m/e 531 (M+1).

EXAMPLE 67

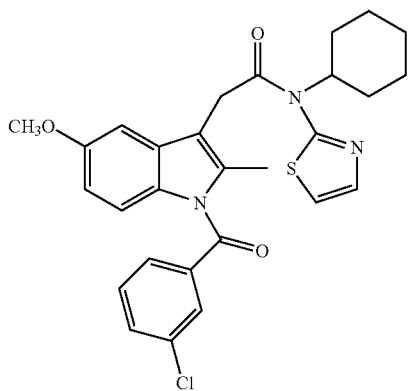

N-Cyclohexyl-N-thiazol-2-yl-1-(3-chlorobenzoyl)-5-methoxy-2-methylindole-3-acetamide Mass Spectrum m/e 522/524 (M+1).

EXAMPLE 68

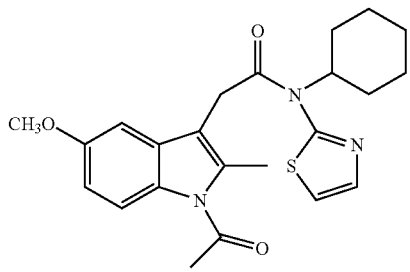

N-Cyclohexyl-N-thiazol-2-yl-1-acetyl-5-methoxy-2-methylindole-3-acetamide

Mass Spectrum m/e 426 (M+1).

EXAMPLE 69

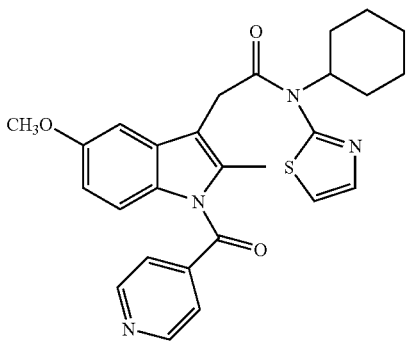

N-Cyclohexyl-N-thiazol-2-yl-1-(pyrid-4-ylcarbonyl)-5-methoxy-2-methylindole-3-acetamide Mass Spectrum m/e 489 (M+1).

EXAMPLE 70

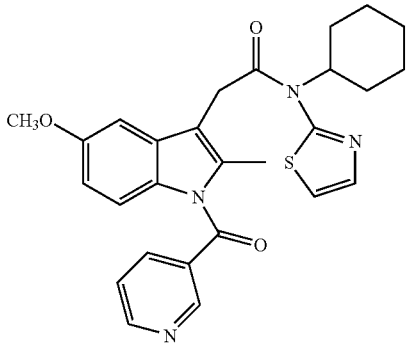

N-Cyclohexyl-N-thiazol-2-yl-1-(pyrid-3-ylcarbonyl)-5-methoxy-2-methylindole-3-acetamide Mass Spectrum m/e 489 (M+1).

EXAMPLE 71

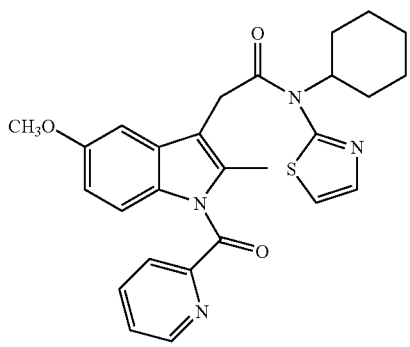

N-Cyclohexyl-N-thiazol-2-yl-1-(pyrid-2-ylcarbonyl)-5-methoxy-2-methylindole-3-acetamide Mass Spectrum m/e 489 (M+1).

EXAMPLE 72

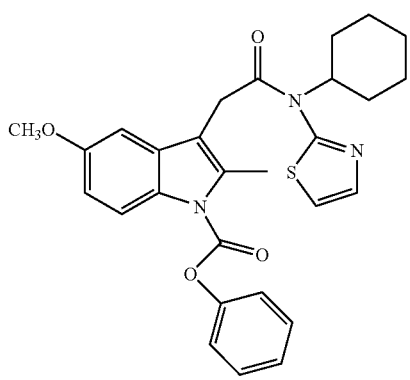

N-Cyclohexyl-N-thiazol-2-yl-1-(phenoxycarbonyl)-5-methoxy-2-methylindole-3-acetamide Mass Spectrum m/e 504 (M+1).

EXAMPLE 73

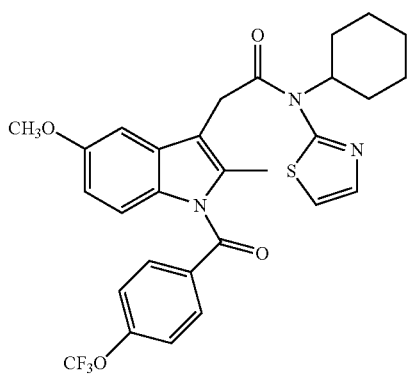

N-Cyclohexyl-N-thiazol-2-yl-1-(4-trifluoromethoxy-benzoyl)-5-methoxy-2-methylindole-3-acetamide Mass Spectrum m/e 572 (M+1).

EXAMPLE 74

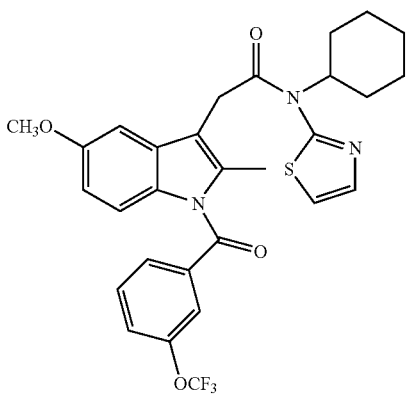

N-Cyclohexyl-N-thiazol-2-yl-1-(3-trifluoromethoxy-benzoyl)-5-methoxy-2-methylindole-3-acetamide Mass Spectrum m/e 572 (M+1).

EXAMPLE 75

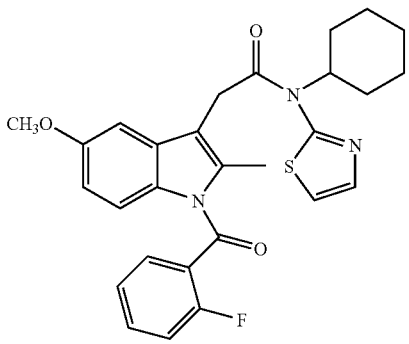

N-Cyclohexyl-N-thiazol-2-yl-1-(2-fluorobenzoyl)-5-methoxy-2-methylindole-3-acetamide Mass Spectrum m/e 506 (M+1).

EXAMPLE 76

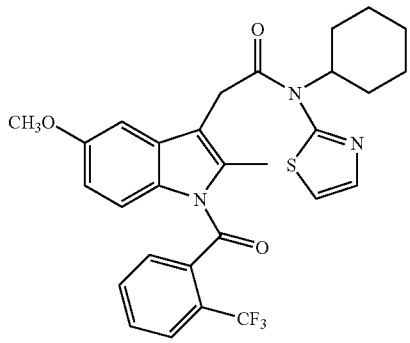

N-Cyclohexyl-N-thiazol-2-yl-1-(2-trifluoromethyl-benzoyl)-5-methoxy-2-methylindole-3-acetamide Mass Spectrum m/e 556 (M+1).

EXAMPLE 77

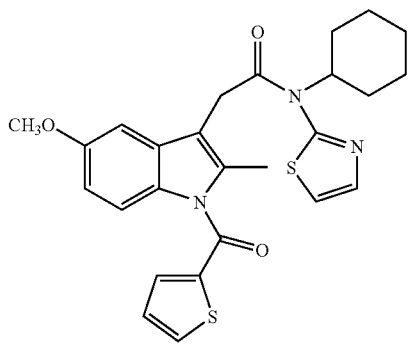

N-Cyclohexyl-N-thiazol-2-yl-1-(thiophen-2-ylcarbonyl)-5-methoxy-2-methylindole-3-acetamide Mass Spectrum m/e 494 (M+1).

EXAMPLE 78

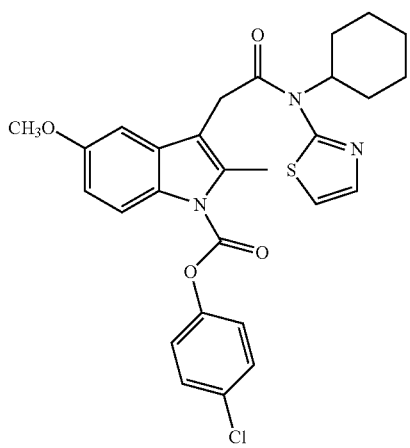

N-Cyclohexyl-N-thiazol-2-yl-1-(4-chlorophenoxycarbonyl)-5-methoxy-2-methylindole-3-acetamide Mass Spectrum m/e 538/540 (M+1).

EXAMPLE 79

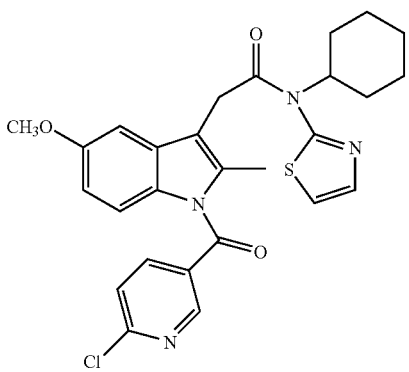

N-Cyclohexyl-N-thiazol-2-yl-1-(2-chloropyrid-5-ylcarbonyl)-5-methoxy-2-methylindole-3-acetamide Mass Spectrum m/e 523/525 (M+1).

EXAMPLE 80

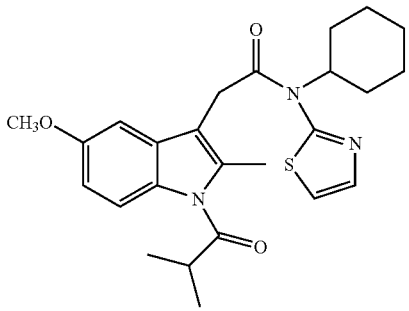

N-Cyclohexyl-N-thiazol-2-yl-1-(i-butanoyl)-5-methoxy-2-methylindole-3-acetamide

Mass Spectrum m/e 454 (M+1).

The following Examples 81 to 86 were prepared from N-Cyclopropylmethyl-N-thiazol-2-yl-5-methoxy-2-methylindole-3-acetamide according to procedures described in Example 58.

EXAMPLE 81

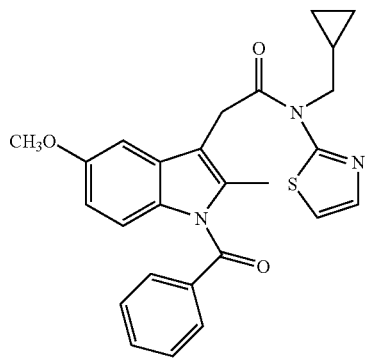

N-Cyclopropylmethyl-N-thiazol-2-yl-1-(benzoyl)-5-methoxy-2-methylindole-3-acetamide Mass Spectrum m/e 460 (M+1).

EXAMPLE 82

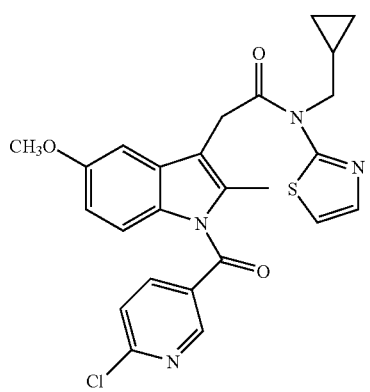

N-Cyclopropylmethyl-N-thiazol-2-yl-1-(4-chloropyrid-5-ylcarbonyl)-5-methoxy-2-methylindole-3-acetamide Mass Spectrum m/e 495/497 (M+1).

EXAMPLE 83

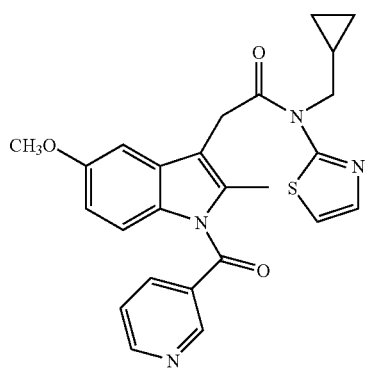

N-Cyclopropylmethyl-N-thiazol-2-yl-1-(pyrid-3-ylcarbonyl)-5-methoxy-2-methylindole-3-acetamide Mass Spectrum m/e 461 (M+1).

EXAMPLE 84

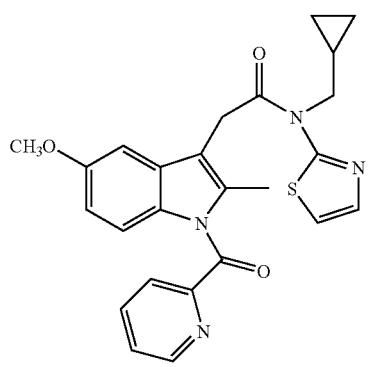

N-Cyclopropylmethyl-N-thiazol-2-yl-1-(pyrid-2-ylcarbonyl)-5-methoxy-2-methylindole-3-acetamide Mass Spectrum m/e 502 (M+CH$_3$CNH$^+$).

EXAMPLE 85

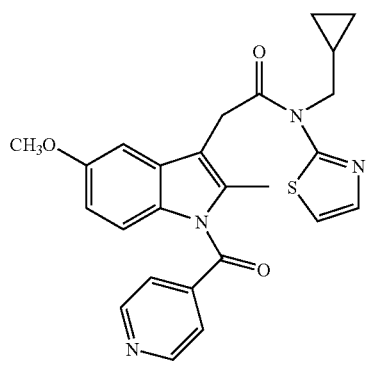

N-Cyclopropylmethyl-N-thiazol-2-yl-1-(pyrid-4-ylcarbonyl)-5-methoxy-2-methylindole-3-acetamide Mass Spectrum m/e 461 (M+1).

EXAMPLE 86

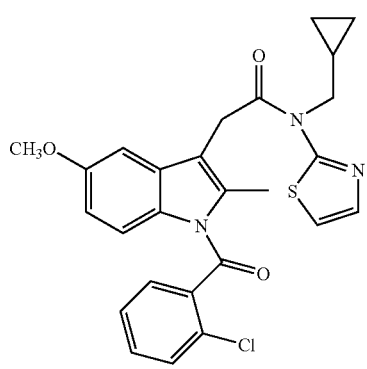

N-Cyclopropylmethyl-N-thiazol-2-yl-1-(2-chlorobenzoyl)-5-methoxy-2-methylindole-3-acetamide Mass Spectrum m/e 494/496 (M+1).

EXAMPLE 87

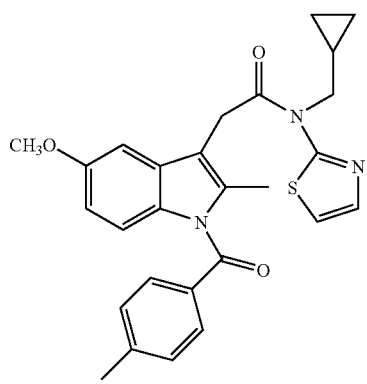

N-Cyclopropylmethyl-N-thiazol-2-yl-1-(4-methylbenzoyl)-5-methoxy-2-methylindole-3-acetamide Mass Spectrum m/e 474 (M+1).

The following Examples 87 to 88 were prepared from N-(2-Morpholinoeth-1-yl)-N-thiazol-2-yl-5-methoxy-2-methylindole-3-acetamide according to procedures described in Example 58.

EXAMPLE 88

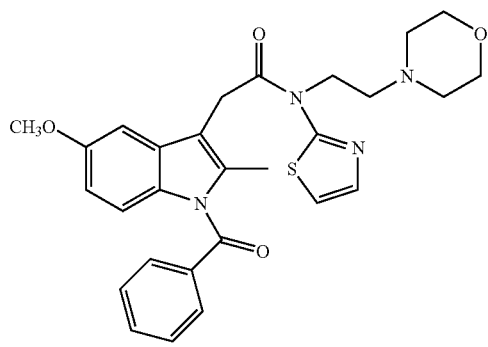

(2-Morpholinoeth-1-yl)-N-thiazol-2-yl-1-(benzoyl)-5-methoxy-2-methylindole-3-acetamide Mass Spectrum m/e 519 (M+1).

EXAMPLE 89

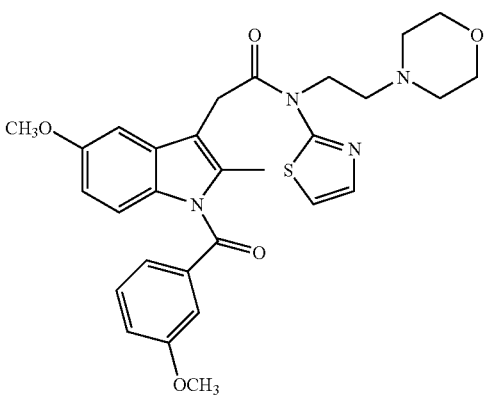

(2-Morpholinoeth-1-yl)-N-thiazol-2-yl-1-(3-methoxybenzoyl)-5-methoxy-2-methylindole-3-acetamide Mass Spectrum m/e 549 (M+1).

The following Examples 89 to 91 were prepared from N-(4-methoxyeth-1-yl)-N-thiazol-2-yl-5-methoxy-2-methylindole-3-acetamide according to procedures described in Example 58.

EXAMPLE 90

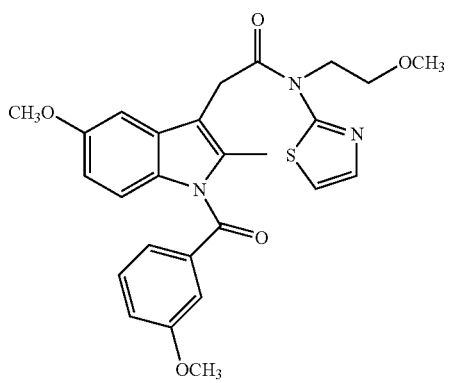

N-(2-methoxyeth-1-yl)-N-thiazol-2-yl-1-(3-methoxybenzoyl)-5-methoxy-2-methylindole-3-acetamide Mass Spectrum m/e 494 (M+1).

EXAMPLE 91

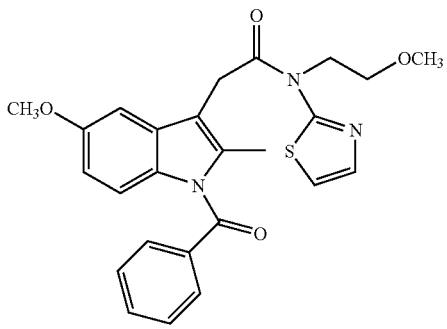

N-(2-methoxyeth-1-yl)-N-thiazol-2-yl-1-(benzoyl)-5-methoxy-2-methylindole-3-acetamide Mass Spectrum m/e 464 (M+1).

EXAMPLE 92

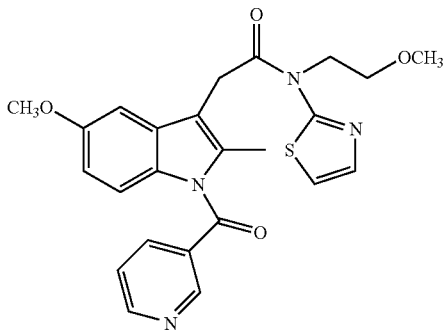

N-(4-methoxyeth-1-yl)-N-thiazol-2-yl-1-(pyrid-3-yl)-5-methoxy-2-methylindole-3-acetamide Mass Spectrum m/e 465 (M+1).

EXAMPLE 93

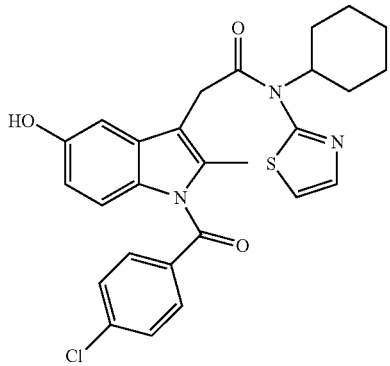

N-Cyclohexyl-N-thiazol-2-yl-1-(2-chlorobenzoyl)-5-hydroxy-2-methylindole-3-acetamide To a solution of 2 g (3.83 mmol) of N-Cyclohexyl-N-thiazol-2-yl-1-(4-chlorobenzoyl)-5-methoxy-2-methylindole-3-acetamide in 20 mL of anhydrous dichloromethane under nitrogen at −78° C. was added dropwise 1.1 mL (11.5 mmol) of boron tribromide over 15 minutes. The reaction was allowed to warm to room temperature and stirred for 20 hr before quenching with water (5 mL). The layers were separated and the organic layer dried (Na$_2$SO$_4$), filtered and evaporated. The residue was chromatographed on silica to give the title compound. $^1$H NMR (DMSO) δ 9.24 (1H, s), 7.79 (2H, bs), 7.70 (4H, m), 6.87 (1H, d), 6.81 (1H, d), 6.59 (1H, dd), 4.43 (1H, bs), 3.40 2.08 (1H, m), 1.77 (4H, m), 1.61 (1H, m), 1.32 (4H, m). 5H concealed by DMSO and water signals.

Mass Spectrum m/e 508/510 (M+1).

EXAMPLE 94

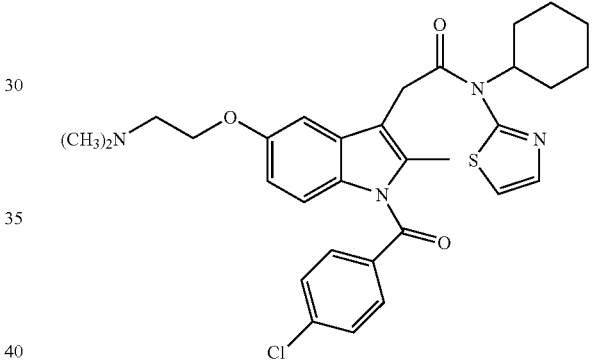

N-Cyclohexyl-N-thiazol-2-yl-1-(2-chlorobenzoyl)-5-(2-dimethylaminoeth-1-yl)hydroxy-2-methylindole-3-acetamide To a solution of 0.05 g (0.1 mmol) of N-Cyclohexyl-N-thiazol-2-yl-1-(4-chlorobenzoyl)-5-hydroxy-2-methylindole-3-acetamide in 2 mL of butan-2-one was added 0.065 g (0.2 mmol) of cesium carbonate and the mixture stirred for 10 min before adding 0.014 g (0.1 mmol) of 2-dimethylaminoethyl chloride. The reaction stirred at room temperature for 48 hr then further alkyl halide was added and the reaction heated at reflux for 4 hr. After evaporation, the residue was chromatographed on silica to give the title compound. $^1$H NMR (CDCl$_3$) δ 8.09 (2H, d), 7.59 (1H, d), 7.42 (2H, d), 7.16 (2H, m), 7.11 (1H, d), 6.88 (1H, d), 4.45 (1H, m), 4.08 (2H, t), 3.56 (2H, bs), 2.49 (2H, t), 2.28 (6H, s), 2.16 (3H, s), 0.9-1.8 (10H, m).

Mass Spectrum m/e 579/581 (M+1).

Example 94 to 99 were prepared from N-Cyclopropylmethyl-N-Thiazol-2-yl-5 methylindole-3-acetamide according to procedures described in Example 58.

EXAMPLE 95

N-Cyclopropylmethyl-N-(thiazol-2-yl)-1-(3-chlorob-ezoyl)-5-methoxy-2-methylindole-3-acetamide Mass Spectrum m/e 494 (M+1).

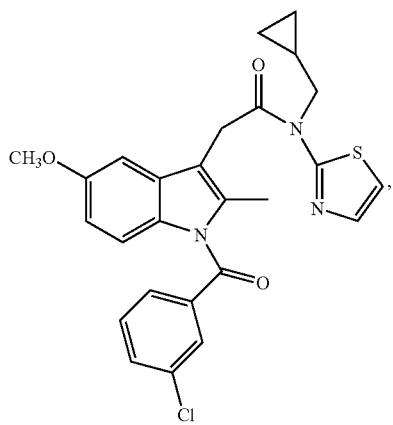

EXAMPLE 96

N-Cyclopropylmethyl-N-(thiazol-2-yl)-1-bezoyl-5-methoxy-2-methylindole-3-acetamide Mass Spectrum m/e 466 (M+1).

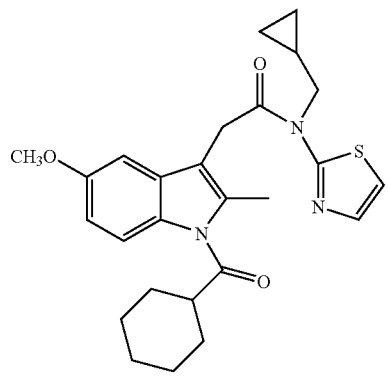

EXAMPLE 97

N-Cyclopropylmethyl-N-(thiazol-2-yl)-1-(3-bromob-ezoyl)-5-methoxy-2-methylindole-3-acetamide Mass Spectrum m/e 538 (M+1).

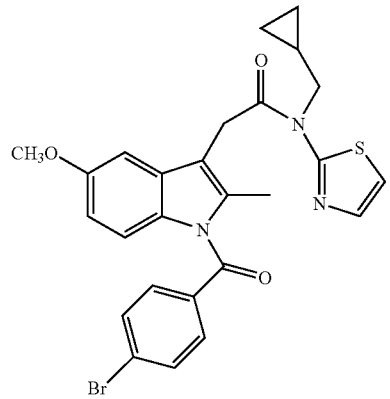

EXAMPLE 98

N-Cyclopropylmethyl-N-(thiazol-2-yl)-1-(3-benzoxylcarbonylbezoyl)-5-methoxy-2-methylindole-3-acetamide Mass Spectrum m/e 594 (M+1).

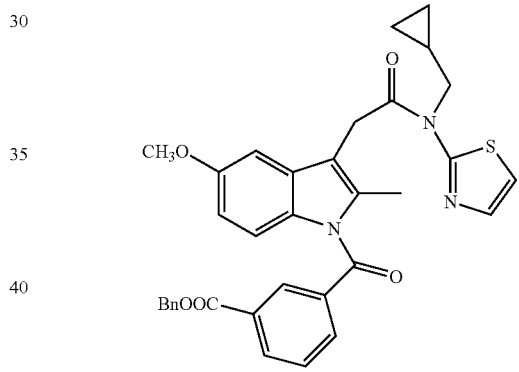

EXAMPLE 99

N-Cyclopropylmethyl-N-(thiazol-2-yl)-1-(methylsulfonyl)-5-methoxy-2-methylindole-3-acetamide Mass Spectrum m/e 434 (M+1).

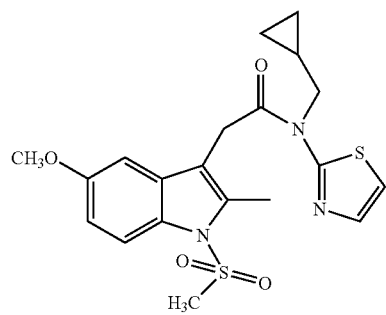

EXAMPLE 100

N-Cyclopropylmethyl-N-(thiazol-2-yl)-1-(methoxy-oxalyl)-5-methoxy-2-methylindole-3-acetamide Mass Spectrum m/e 442 (M+1).

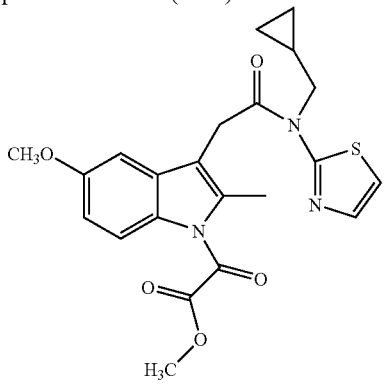

EXAMPLE 101

N-Cyclopropylmethyl-N-(thiazol-2-yl)-1-(4-hydroxylcarbonylbezoyl)-5-methoxy-2-methylindole-3-acetamide Example 100 was prepared from N-Cyclopropylmethyl-N-Thiazol-2-yl-5-methylindole-3-acetamide with 1,4-chlorocarbonylbenzene according to procedures described in Example 58, followed by in situ hydrolysis.

Mass Spectrum m/e 504 (M+1).

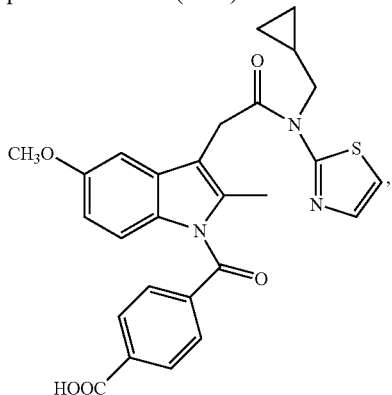

EXAMPLE 102

N-Cyclopropylmethyl-N-(thiazol-2-yl)-1-(3-hydroxylcarbonylbezoyl)-5-methoxy-2-methylindole-3-acetamide To a solution of 6.4 mg example 97 in 1 mL of EtOAc was added 5 mg Pd(OH)$_2$/C. The reaction mixture was hydrogenated under a balloon of hydrogen for 4 hr. Filtered off the catalyst through a layer of Celite. The solvent was removed to give the title compound.

Mass Spectrum m/e 504 (M+1).

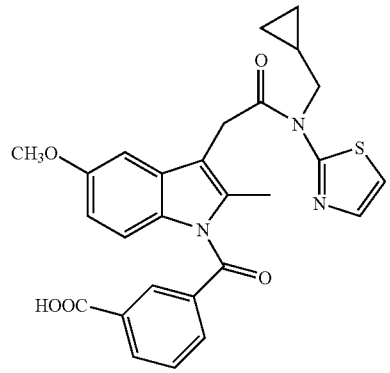

EXAMPLE 103

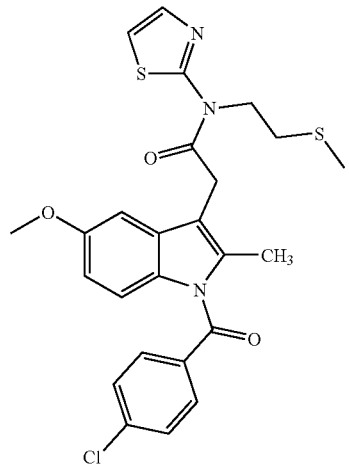

N-(2-Methanethioeth-1-yl)-N-(thiazol-2-yl)-1-(4-chlorobenzoyl)-5-methoxy-2-methylindole-3-acetamide Prepared as described in Example 48.
Mass Spectrum m/e 514/516 (M+1).

EXAMPLE 104

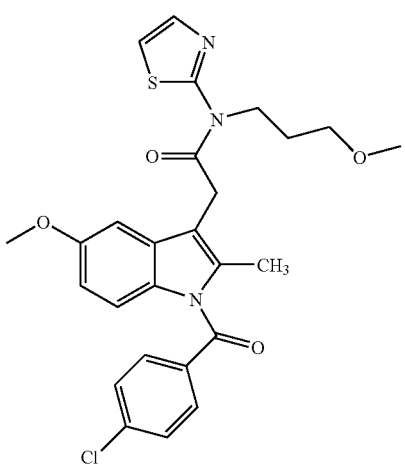

N-(3-Methoxyprop-1-yl)-N-(thiazol-2-yl)-1-(4-chlorobenzoyl)-5-methoxy-2-methylindole-3-acetamide Prepared as described in Example 48.
Mass Spectrum m/e 512/514 (M+1).

EXAMPLE 105

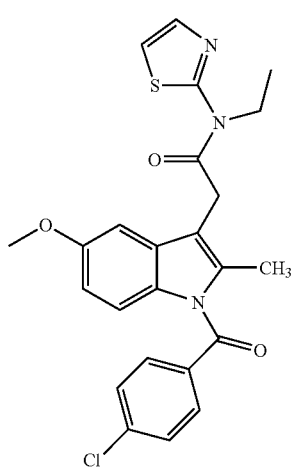

N-Ethyl-N-(thiazol-2-yl)-1-(4-chlorobenzoyl)-5-methoxy-2-methylindole-3-acetamide Prepared as described in Example 1.
Mass Spectrum m/e 468/470 (M+1).
1H NMR (CDCl3): 7.70 (2H, d), 7.55 (1H, d), 7.50 (2H, d), 7.03 (1H, bs), 6.94 (1H, d), 6.83 (1H, d), 6.68 (1H, dd), 4.40 (2H, bs), 4.04 (2H, s), 3.82 (3H, s), 2.44 (3H, s), 1.45 (3H, bt).

EXAMPLE 106

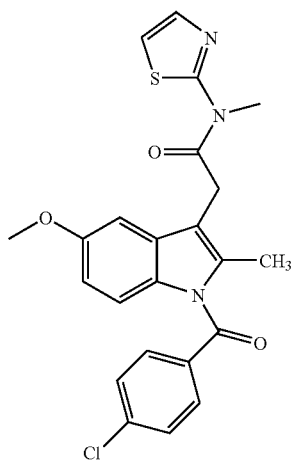

N-Ethyl-N-(thiazol-2-yl)-1-(4-chlorobenzoyl)-5-methoxy-2-methylindole-3-acetamide Prepared as described in Example 52.
Mass Spectrum m/e 454/456 (M+1).
1H NMR (CDCl3): 7.70 (2H, d), 7.58 (1H, bs), 7.50 (2H, d), 7.06 (1H, bs), 6.92 (1H, d), 6.83 (1H, d), 6.68 (1H, dd), 4.06 (2H, s), 3.85 (3H, s), 3.82 (3H, s), 2.44 (3H, s).

EXAMPLE 107

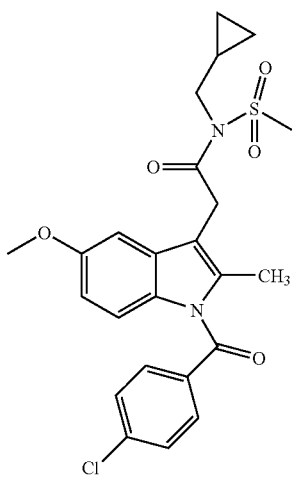

N-Cyclopropylmethyl-N-methanesulfonly-1-(4-chlorobenzoyl)-5-methoxy-2-methylindole-3-acetamide Step A: N-methanesulfonly-1-(4-chlorobenzoyl)-5-methoxy-2-methylindole-3-acetamide To a solution of 1-(4-chlorobenzoyl)-5-methoxy-2-methylindole-3-acetic acid (360 mg) in THF was added carbonyldiimidazole (180 mg) at rt. After stirring for a couple of hours, methansulfonamide (140 mg) and 1,8-diazabicyclo[5.4.0]undec-7-ene (0.22 ml) were added to reaction mixture. The reaction was monitored by LC-MS. After completed reaction, the mixture was concentrated and purified by crystallization (hexanes/ethyl acetate) to give desired coupling product (272 mg).

1H NMR (CDCl3): 8.18 (1H, bs), 7.71 (2H, d), 7.52 (2H, d), 6.88 (1H, d), 6.85 (1H, d), 6.73 (1H, dd), 3.84 (2H, s), 3.78 (3H, s), 3.28 (3H, s), 2.44 (3H, s).

To a solution of N-methanesulfonly-1-(4-chlorobenzoyl)-5-methoxy-2-methylindole-3-acetamide (44 mg) in TBF was added diethyl azodicarboxylate (0.047 ml), triphenyl phosphine (100 mg) and cyclopropylmethanol (0.024 ml). The reaction was monitored by LC-MS. After completed reaction, the mixture was concentrated and purified by silica gel (hexanes/ethyl acetate) to give desired product (13 mg).

Mass Spectrum m/e 489/491 (M+1).
1H NMR (CDCl3): 7.69 (2H, d), 7.50 (2H, d), 6.92 (1H, d), 6.86 (1H, d), 6.69 (1H, dd), 4.10 (2H, s), 3.84 (3H, s), 3.81 (2H, d), 3.33 (3H, s), 2.41 (3H, s), 1.11 (1H, m), 0.64 (2H, m), 0.47 (2H, m).

Functional Assays

A. Maxi-K Channel

The activity of the compounds can also be quantified by the following assay.

The identification of inhibitors of the Maxi-K channel is based on the ability of expressed Maxi-K channels to set cellular resting potential after transfection of both alpha and beta1 subunits of the channel in BEK-293 cells and after being incubated with potassium channel blockers that selectively eliminate the endogenous potassium conductances of HEK-293 cells. In the absence of maxi-K channel inhibitors, the transfected HEK-293 cells display a hyperpolarized membrane potential, negative inside, close to $E_K$ (−80 mV) which is a consequence of the activity of the maxi-K channel. Blockade of the Maxi-K channel by incubation with maxi-K channel blockers will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$).

Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization, which determines if a test compound actively blocks the maxi-K channel.

The HEK-293 cells were obtained from the American Type Culture Collection, 12301 Parklawn Drive, Rockville, Md., 20852 under accession number ATCC CRL-1573. Any restrictions relating to public access to the microorganism shall be irrevocably removed upon patent issuance.

Transfection of the alpha and beta1 subunits of the maxi-K channel in HEK-293 cells was carried out as follows: HEK-293 cells were plated in 100 mm tissue culture treated dishes at a density of $3 \times 10^6$ cells per dish, and a total of five dishes were prepared. Cells were grown in a medium consisting of Dulbecco's Modified Eagle Medium (DMEM) supplemented with 10% Fetal Bovine serum, 1× L-Glutamine, and 1× Penicillin/Streptomycin, at 37° C., 10% $CO_2$. For transfection with Maxi-K hα(pCIneo) and Maxi-K hβ1(pIRESpuro) DNAs, 150 µl FuGENE6™ was added dropwise into 10 ml of serum free/phenol-red free DMEM and allowed to incubate at room temperature for 5 minutes. Then, the FuGENE6™ solution was added dropwise to a DNA solution containing 25 µg of each plasmid DNA, and incubated at room temperature for 30 minutes. After the incubation period, 2 ml of the FuGENE6™/DNA solution was added dropwise to each plate of cells and the cells were allowed to grow two days under the same conditions as described above. At the end of the second day, cells were put under selection media which consisted of DMEM supplemented with both 600 µg/ml G418 and 0.75 µg/ml puromycin. Cells were grown until separate colonies were formed. Five colonies were collected and transferred to a 6 well tissue culture treated dish. A total of 75 colonies were collected. Cells were allowed to grow until a confluent monolayer was obtained. Cells were then tested for the presence of maxi-K channel alpha and beta1 subunits using an assay that monitors binding of $^{125}$I-iberiotoxin-D19Y/Y36F to the channel. Cells expressing $^{125}$I-iberiotoxin-D19Y/Y36F binding activity were then evaluated in a functional assay that monitors the capability of maxi-K channels to control the membrane potential of transfected HEK-293 cells using fluorescence resonance energy transfer (FRET) ABS technology with a VIPR instrument. The colony giving the largest signal to noise ratio was subjected to limiting dilution. For this, cells were resuspended at approximately 5 cells/ml, and 200 µl were plated in individual wells in a 96 well tissue culture treated plate, to add ca. one cell per well. A total of two 96 well plates were made. When a confluent monolayer was formed, the cells were transferred to 6 well tissue culture treated plates. A total of 62 wells were transferred. When a confluent monolayer was obtained, cells were tested using the FRET-functional assay. Transfected cells giving the best signal to noise ratio were identified and used in subsequent functional assays.

For Functional Assays:

The transfected cells (2E+06 Cells/mL) are then plated on 96-well poly-D-lysine plates at a density of about 100,000 cells/well and incubated for about 16 to about 24 hours. The medium is aspirated of the cells and the cells washed one time with 100 µl of Dulbecco's phosphate buffered saline (D-PBS). One hundred microliters of about 9 µM coumarin ($CC_2DMPE$)-0.02% pluronic-127 in D-PBS per well is added and the wells are incubated in the dark for about 30 minutes. The cells are washed two times with 100 µl of Dulbecco's phosphate-buffered saline and 100 µl of about 4.5 µM of oxanol ($DiSBAC_2(3)$) in (mM) 140 NaCl, 0.1 KCl, 2 $CaCl_2$, 1 $MgCl_2$, 20 Hepes-NaOH, pH 7.4, 10 glucose is added. Three micromolar of an inhibitor of endogenous potassium conductance of HEK-293 cells is added. A maxi-K channel blocker is added (about 0.01 micromolar to about 10 micromolar) and the cells are incubated at room temperature in the dark for about 30 minutes.

The plates are loaded into a voltage/ion probe reader (VIPR) instrument, and the fluorescence emission of both $CC_2DMPE$ and $DiSBAC_2(3)$ are recorded for 10 sec. At this point, 100 µl of high-potassium solution (mM): 140 KCl, 2 $CaCl_2$, 1 $MgCl_2$, 20 Hepes-KOH, pH 7.4, 10 glucose are added and the fluorescence emission of both dyes recorded for an additional 10 sec. The ratio $CC_2DMPE/DiSBAC_2(3)$, before addition of high-potassium solution equals 1. In the absence of maxi-K channel inhibitor, the ratio after addition of high-potassium solution varies between 1.65-2.0. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with $IC_{50}$'s in the range of about 1 nM to about 20 µM, more preferably from about 10 nM to about 500 nM.

B. Electrophysiological Assays of Compound Effects on High-conductance Calcium-activated Potassium Channels Methods:

Patch clamp recordings of currents flowing through large-conductance calcium-activated potassium (maxi-K) channels were made from membrane patches excised from CHO cells constitutively expressing the α-subunit of the maxi-K channel or HEK293 cells constitutively expressing both α- and β-subunits using conventional techniques (Hamill et al., 1981, Pflügers Archiv. 391, 85-100) at room temperature. Glass capillary tubing (Garner #7052 or Drummond custom borosilicate glass 1-014-1320) was pulled in two stages to yield micropipettes with tip diameters of approximately 1-2 microns. Pipettes were typically filled with solutions containing (mM): 150 KCl, 10 Hepes (4-(2-hydroxyethyl)-1-piperazine methanesulfonic acid), 1 Mg, 0.01 Ca, and adjusted to pH 7.20 with KOH. After forming a high resistance (>$10^9$ ohms) seal between the plasma membrane and the pipette, the pipette was withdrawn from the cell, forming an excised inside-out membrane patch. The patch was excised into a bath solution containing (mM): 150 KCl, 10 Hepes, 5 EGTA (ethylene glycol bis(β-aminoethyl ether)-N,N,N',N'-tetraacetic acid), sufficient Ca to yield a free Ca concentration of 1-5 μM, and the pH was adjusted to 7.2 with KOH. For example, 4.193 mM Ca was added to give a free concentration of 1 μM at 22° C. An EPC9 amplifier (HEKA Elektronic, Lambrect, Germany) was used to control the voltage and to measure the currents flowing across the membrane patch. The input to the headstage was connected to the pipette solution with a Ag/AgCl wire, and the amplifier ground was connected to the bath solution with a Ag/AgCl wire covered with a tube filled with agar dissolved in 0.2 M KCl. The identity of maxi-K currents was confirmed by the sensitivity of channel open probability to membrane potential and intracellular calcium concentration.

Data acquisition was controlled by PULSE software (HEKA Elektronic) and stored on the hard drive of a MacIntosh computer (Apple Computers) for later analysis using PULSEFIT (HEKA Elektronic) and Igor (Wavemetrics, Oswego, Oreg.) software.

RESULTS

The effects of the compounds of the present invention on maxi-K channels were examined in excised inside-out membrane patches with constant superfusion of bath solution. The membrane potential was held at −80 mV and brief (100-200 ms) voltage steps to positive membrane potentials (typically +50 mV) were applied once per 15 seconds to transiently open maxi-K channels. As a positive control in each experiment, maxi-K currents were eliminated at pulse potentials after the patch was transiently exposed to a low concentration of calcium (<10 nM) made by adding 1 mM EGTA to the standard bath solution with no added calcium. The fraction of channels blocked in each experiment was calculated from the reduction in peak current caused by application of the specified compound to the internal side of the membrane patch. Compound was applied until a steady state level of block was achieved. $K_I$ values for channel block were calculated by fitting the fractional block obtained at each compound concentration with a Hill equation. The $K_I$ values for channel block by the compounds described in the present invention range from 0.01 nM to greater than 10 μM.

What is claimed is:
1. A compound of the structural formula I:

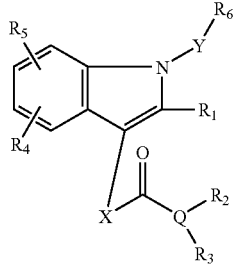

Formula I or a pharmaceutically acceptable salt, enantiomer, diastereomer or mixture thereof:
wherein,
R represents hydrogen, or $C_{1-6}$ alkyl;
$R_1$ represents hydrogen or $C_{1-6}$ alkyl, $CF_3$, $C_{1-6}$ alkoxy, OH, $COR^c$, $CO_2R_8$, $CONHCH_2CO_2R$, $N(R)_2$, said alkyl and alkoxy optionally substituted with 1-3 groups selected from $R^b$;
X represents —$(CHR_7)_p$—;

Y represents —$CO(CH_2)_n$—, or —$CH(OR)$—;
Q represents N, CRy, or O, wherein $R_2$ is absent when Q is O;
Ry represents H, or $C_{1-6}$ alkyl;
$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2C_{6-10}$ aryl, $NO_2$, CN or —$C(O)N(R)_2$;
$R_2$ represents hydrogen, $C_{1-10}$ alkyl, $C_{1-6}$ alkylSR, —$(CH_2)_nO(CH_2)_mOR$, —$(CH_2)_nC_{1-6}$ alkoxy, —$(CH_2)_nC_{3-8}$ cycloalkyl, —$(CH_2)_nC_{3-10}$ heterocyclyl, —$(CH_2)_nC_{5-10}$ heteroaryl, —$N(R)_2$, —COOR, or —$(CH_2)_nC_{6-10}$ aryl, said alkyl, heterocyclyl, aryl or heteroaryl optionally substituted with 1-3 groups selected from $R^a$;
$R_3$ represents hydrogen, $C_{1-10}$ alkyl, —$(CH_2)_nC_{3-8}$ cycloalkyl, —$(CH_2)_nC_{3-10}$ heterocyclyl, —$(CH_2)_nC_{5-10}$ heteroaryl, —$(CH_2)_nCOOR$, —$(CH_2)_nC_{6-10}$ aryl, —$(CH_2)_nNHR_8$, —$(CH_2)_nN(R)_2$, —$(CH_2)_nN(R_8)_2$, —$(CH_2)_nNHCOOR$, —$(CH_2)_nN(R_8)CO_2R$, —$(CH_2)_nN(R_8)COR$, —$(CH_2)_nNHCOR$, —$(CH_2)_nCONH(R_8)$, aryl, —$(CH_2)_nC_{1-6}$—OR, $CF_3$, —$(CH_2)_nSO_2R$, —$(CH_2)_nSO_2N(R)_2$, —$(CH_2)_nCON(R)_2$, —$(CH_2)_nCONHC(R)_3$, —$(CH_2)_nCONHC(R)_2CO_2R$, —$(CH_2)_nCOR_8$, nitro, cyano or halogen, said alkyl, alkoxy, heterocyclyl, aryl or heteroaryl optionally substituted with 1-3 groups of $R^a$, provided $R_3$ is not pyridinyl or substituted thiazolyl when $R_2$ is hydrogen and Q is N or $R_3$ is not pyridinyl when Q is O;
or, when Q is N, $R_2$ and $R_3$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;
$R_4$ and $R_5$ independently represent hydrogen, $C_{1-6}$ alkoxy, OH, $C_{1-6}$ alkyl, COOR, $SO_3H$, $C_{1-6}$ alkylcarbonyl, $S(O)_qR^y$, —$O(CH_2)_nN(R)_2$, —$O(CH_2)_nCO_2R$, —OPO$(OH)_2$, $CF_3$, —$N(R)_2$, nitro, cyano, $C_{1-6}$ alkylamino, or halogen;
$R_6$ represents hydrogen, $C_{1-10}$ alkyl, —$(CH_2)_nC_{6-10}$ aryl, —$NH(CH_2)_nC_{6-10}$ aryl, —$(CH_2)_nC_{5-10}$ heteroaryl, —$NH(CH_2)_nC_{5-10}$ heteroaryl, $(C_{6-10}$ aryl)O—, —$(CH_2)_nC_{3-10}$ heterocyclyl, —$(CH_2)_nC_{3-8}$ cycloalkyl, —COOR, —$C(O)CO_2R$, said aryl, heteroaryl, heterocyclyl and alkyl optionally substituted with 1-3 groups selected from $R^a$;
$R_7$ represents hydrogen, $C_{1-6}$ alkyl, —$(CH_2)_nCOOR$ or —$(CH_2)_nN(R)_2$,
$R_8$ represents —$(CH_2)_nC_{3-8}$ cycloalkyl, —$(CH_2)_{n\,3-10}$ heterocyclyl, $C_{1-6}$ alkoxy or —$(CH_2)_nC_{5-10}$ heteroaryl, —$(CH_2)_nC_{6-10}$ aryl said heterocyclyl, aryl or heteroaryl optionally substituted with 1-3 groups selected from $R^a$;
$R^a$ represents F, Cl, Br, I, $CF_3$, $N(R)_2$, $NO_2$, CN, —$(CH_2)_nCOR_8$, —$(CH_2)_nCONHR_8$, —$(CH_2)_nCON(R_8)_2$, —$O(CH_2)_nCOOR$, —$NH(CH_2)_nOR$, —COOR, —$OCF_3$, —NHCOR, —$SO_2R$, —$SO_2NR_2$, —SR, $(C_1$-$C_6$ alkyl)O—, —$(CH_2)_nO(CH_2)_mOR$, —$(CH_2)_nC_{1-6}$ alkoxy, (aryl)O—, —OH, $(C_1$-$C_6$ alkyl)$S(O)_m$—, $H_2N$—C(NH)—, $(C_1$-$C_6$ alkyl)C(O)—, $(C_1$-$C_6$ alkyl)OC(O)NH—, —$(C_1$-$C_6$ alkyl)NR$_w$(CH$_2$)$_n$C$_{3-10}$ heterocyclyl-R$_w$, —$(C_1$-$C_6$ alkyl)O(CH$_2$)$_n$C$_{3-10}$ heterocyclyl-R$_w$, —$(C_1$-$C_6$ alkyl)S(CH$_2$)$_n$C$_{3-10}$ heterocyclyl -R$_w$, —$(C_1$-$C_6$ alkyl)-C$_{3-10}$ heterocyclyl-R$_w$, —$(CH_2)_n$-Z$_1$-C($=Z^2$)N(R)$_2$, —$(C_{2-6}$ alkenyl)NR$_w$(CH$_2$)$_n$C$_{3-10}$ heterocyclyl-R$_w$, —$(C_{2-6}$ alkenyl)O(CH$_2$)$_n$C$_{3-10}$ heterocyclyl-R$_w$, —$(C_{2-6}$ alkenyl)S(CH$_2$)$_n$C$_{3-10}$ heterocyclyl-R$_w$, —$(C_{2-6}$ alkenyl)-C$_{3-10}$ heterocyclyl-R$_w$, —$(C_{2-6}$ alkenyl)-Z$^1$-C($=Z^2$)N(R)$_2$, —$(CH_2)_nSO_2R$, —$(CH_2)_n$ SO₃H, —(CH₂)ₙPO(OR)₂, cyclohexyl, morpholinyl, piperidyl, pyrrolidinyl, thiophenyl, phenyl, pyridyl, imidazolyl, oxazolyl, isoxazolyl, thiazolyl, thienyl, furyl, isothiazolyl, C$_{2-6}$ alkenyl, and C$_1$-C$_{10}$ alkyl, said alkyl, alkenyl, alkoxy, phenyl, pyridyl, imidazolyl, oxazolyl, isoxazolyl, thiazolyl, thienyl, furyl, and isothiazolyl optionally substituted with 1-3 groups selected from C$_1$-C$_6$ alkyl, and COOR;

Z$^1$ and Z$^2$ independently represents NR$_w$, O, CH$_2$, or S;

R$^b$ represents C$_{1-6}$ alkyl, —COOR, —SO$_3$R, —OPO(OH)$_2$, —(CH$_2$)$_n$C$_{6-10}$ aryl, or —(CH$_2$)$_n$C$_{5-10}$ heteroaryl;

R$^c$ represents hydrogen, C$_{1-6}$ alkyl, or —(CH$_2$)$_n$C$_{6-10}$ aryl;

m is 0-3;

n is 0-3;

q is 0-2; and p is 0-1.

2. A compound of the structural formula I wherein X is CHR$_7$.

3. A compound according to claim 1 wherein Y is —CO(CH$_2$)$_n$.

4. A compound according to claim 1 wherein Y is CH(OR).

5. A compound according to claim 1 wherein Q is N.

6. A compound according to claim 1 wherein Q is CH.

7. A compound according to claim 2 wherein R$_6$ is (CH$_2$)$_n$C$_{6-10}$ aryl, (CH$_2$)$_n$C$_{5-10}$ heteroaryl, (CH$_2$)$_n$C$_{3-10}$ heterocyclyl, or (CH$_2$)$_n$C$_{3-8}$ cycloalkyl, said aryl, heteroaryl, heterocyclyl and alkyl optionally substituted with 1 to 3 groups of R$^a$.

8. A compound according to claim 6 wherein R$_7$ is hydrogen or C$_{1-6}$ alkyl.

9. A compound according to claim 6 wherein Q is N and n is 0.

10. A compound according to claim 1 wherein Y is —CO(CH$_2$)$_n$, Q is N, n is 0, R$_2$ is C$_{1-10}$ alkyl or C$_{1-6}$ alkylOH and R$_3$ is (CH$_2$)$_n$C$_{3-10}$ heterocyclyl, said heterocyclyl and alkyl optionally substituted with 1 to 3 groups of R$^a$.

11. A composition comprising a pharmaceutically acceptable carrier and an effective amount of a compound according to claim 1.

12. A compound according to claim 1 which is:

TABLE 1

TABLE 1-continued

Wherein R represents:

—NH(CH$_2$)$_3$NHCO$_2$X,   —NH(CH$_2$)$_2$NHCO$_2$X, or

—NHC$_{1-6}$alkyl;

n is 0 to 3;
X, Y and Z, independently represent hydrogen or C$_{1-6}$ alkyl; and
Rc represents hydrogen, halogen, C$_{1-6}$ alkyl, CF3, OCF3, N(CH3)3, COC$_{1-6}$ alkyl, or methoxy; or a pharmaceutically acceptable salt, enantiomer, diastereomer or mixture thereof.

13. The compound according to claim 1 which

TABLE 2 wherein R represents:

TABLE 2-continued wherein R represents:

n is 0 to 3; s is 1-5;
X represents hydrogen or C$_{1-6}$ alkyl;
R$^b$ and R$^a$ independently represent hydrogen, methoxy, CO$_2$X, NHAc, or C$_{1-6}$ alkyl;
R$^c$ represents hydrogen, halogen, C$_{1-6}$ alkyl, CF$_3$, OCF$_3$, N(CH$_3$)$_2$, COC$_{1-6}$ alkyl, or methoxy or a pharmaceutically acceptable salt, enantiomer, diastereomer or mixture thereof.

14. The compound according to claim 1 which is:

TABLE 3

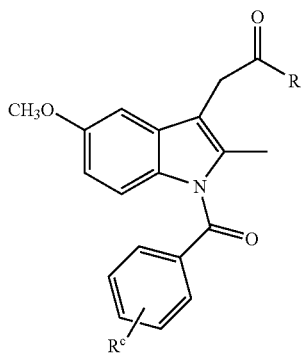

wherein R represents:

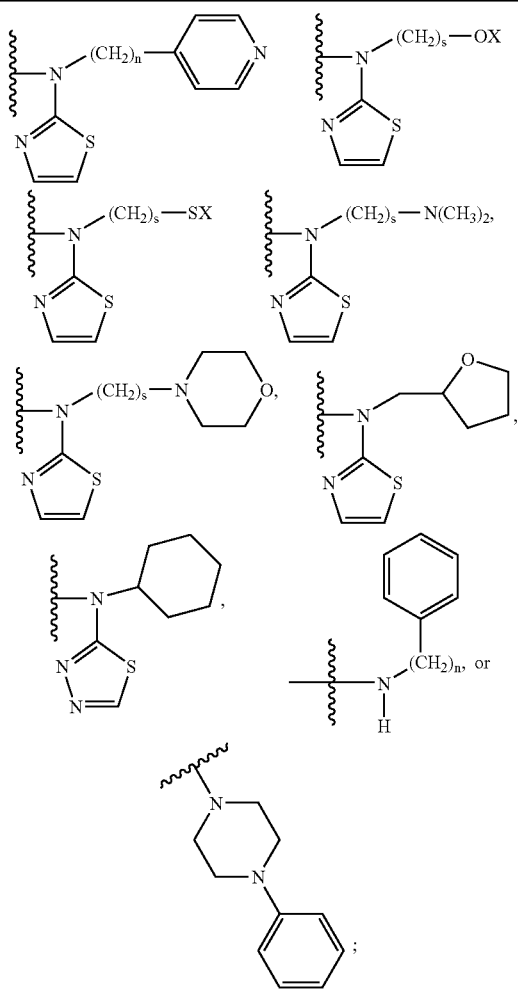

n is 0 to 3; s is 1-5;
X represents hydrogen or $C_{1-6}$ alkyl; and
$R^c$ represents hydrogen, halogen, $C_{1-6}$ alkyl, $CF_3$, $OCF_3$, $N(CH_3)_2$, $COC_{1-6}$ alkyl, or methoxy or a pharamceutically acceptable salt, enantiomer, diastereomer or mixture thereof.

15. The compound according to claim 1 which is:

TABLE 4

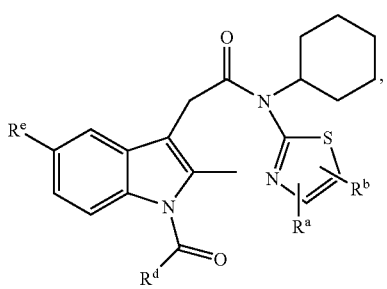

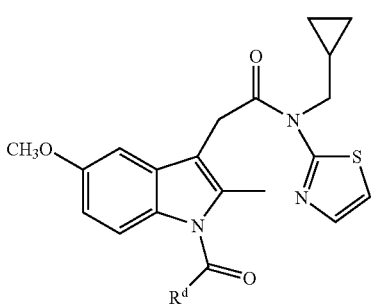

or

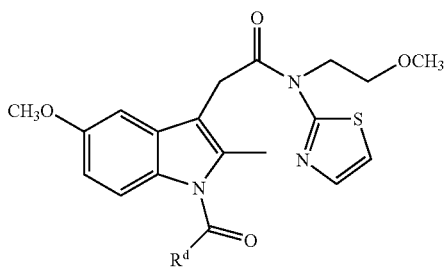

wherein:
$R^b$ and $R^a$ independently represent hydrogen, methoxy, $CO_2X$, NHAc, or $C_{1-6}$ alkyl;
$R^d$ represents C1-6 alkyl, pyridinyl, —O-phenyl, phenyl, thienyl, said pyridinyl and phenyl optionally substituted with 1-3 halogen, $CF_3$, $OCF_3$, $N(CH_3)_2$, methoxy or C1-6 alkyl; and
$R^e$ represents methoxy, $O(CH_2)_2N(CH_3)_2$, or OH; or a pharmaceutically acceptable salt, enantiomer, diastereomer or mixture thereof.

* * * * *